United States Patent
Palis et al.

(10) Patent No.: US 10,260,043 B2
(45) Date of Patent: Apr. 16, 2019

(54) HUMAN EXTENSIVELY SELF-RENEWING ERYTHROBLASTS (ESRE)

(71) Applicant: UNIVERSITY OF ROCHESTER, Rochester, NY (US)

(72) Inventors: James Palis, Rochester, NY (US); Samantha England, Marseilles (FR); Ah Ram Kim, Rochester, NY (US)

(73) Assignee: UNIVERSITY OF ROCHESTER, Rochester, NY (US)

(*) Notice: Subject to any disclaimer, the term of this patent is extended or adjusted under 35 U.S.C. 154(b) by 25 days.

(21) Appl. No.: 14/888,110

(22) PCT Filed: May 15, 2014

(86) PCT No.: PCT/US2014/038075
§ 371 (c)(1),
(2) Date: Oct. 30, 2015

(87) PCT Pub. No.: WO2014/186508
PCT Pub. Date: Nov. 20, 2014

(65) Prior Publication Data
US 2016/0068810 A1    Mar. 10, 2016

Related U.S. Application Data

(60) Provisional application No. 61/823,677, filed on May 15, 2013.

(51) Int. Cl.
*A61K 35/18* (2015.01)
*C12N 5/078* (2010.01)

(52) U.S. Cl.
CPC ............ *C12N 5/0641* (2013.01); *A61K 35/18* (2013.01); *C12N 2500/36* (2013.01); *C12N 2500/90* (2013.01); *C12N 2501/125* (2013.01); *C12N 2501/14* (2013.01); *C12N 2501/33* (2013.01); *C12N 2501/39* (2013.01); *C12N 2506/02* (2013.01); *C12N 2510/00* (2013.01)

(58) Field of Classification Search
None
See application file for complete search history.

(56) References Cited

U.S. PATENT DOCUMENTS

| 5,905,041 A | 5/1999 | Beug et al. |
| 6,361,998 B1 | 4/2002 | Bell et al. |
| 2008/0008651 A1 | 1/2008 | Engel |
| 2013/0059783 A1 | 3/2013 | Flygare et al. |

FOREIGN PATENT DOCUMENTS

WO    2007095064 A2    8/2007

OTHER PUBLICATIONS

England et al., 2011, "Immature erythroblasts with extensive ex vivo self-renewal capacity emerge from the early mammalian fetus", Blood, 117(9): 2708-2717.
Iwama et al., 2004, "Enhanced Self-Renewal of Hematopoietic Stem Cells Mediated by the Polycomb Gene Product Bmi-1", Immunity, 21(6): 843-851.
Chang et al., 2006, "Stem cell-derived erythroid cells mediate long-term systemic protein delivery", Nat Biotechnol, 24(8): 1017-1021.
Moon et al., 2011, "Reprogramming fibroblasts into induced pluripotent stem cells with Bmi1", Cell Res, 21:1305-1315.
Nachtergaele et al., 2012, "Oxysterols are allosteric activators of the oncoprotein Smoothened", Nat. Chem. Biol, 8:211-220.
Wang et al., 2012, "Sonic hedgehog regulates Bmi1 in human medulloblastoma brain tumor-initiating cells", Oncogene, 31:187-199.
Olivier et al., 2006, "Large-Scale Production of Embryonic Red Blood Cells From Human Embryonic Stem Cells", Exp. Hematol, 1635-1642.
Kyba et al., 2002, "HoxB4 confers definitive lymphoid-myeloid engraftment potential on embryonic stem cell and yolk sac hematopoietic progenitors", Cell, 109:29-37.
Paluru et al., 2014, "The negative impact of Wnt signaling on megakaryocyte and primitive erythroid progenitors derived from human embryonic stem cells", Stem Cell Res, 12:441-451.
Vodyanik et al., 2005, "Human embryonic stem cell—derived CD34+ cells: efficient production in the coculture with OP9 stromal cells and analysis of lymphohematopoietic potential", Blood, 105:617-626.
Koury et al., 1990, "Erythropoietin retards DNA breakdown and prevents programmed death in erythroid progenitor cells",Science, 248:378-381.
Von Lindern et al., 1999, "The Glucocorticoid Receptor Cooperates With the Erythropoietin Receptor and c-Kit to Enhance and Sustain Proliferation of Erythroid Progenitors in Vitro", Blood, 94:550-559.
Panzenbock et al., 1998, "Growth and Differentiation of Human Stem Cell Factor/Erythropoietin-Dependent Erythroid Progenitor Cells in Vitro", Blood, 92:3658-3668.
Muller et al., 1994, "Development of hematopoietic stem cell activity in the mouse embryo", Immunity, 1:291-301.
Ivanovs et al., 2011, "Highly potent human hematopoietic stem cells first emerge in the intraembryonic aorta-gonad-mesonephros region", J Exp Med, 208: 2417-2427.
Palis et al., 1999, "Development of erythroid and myeloid progenitors in the yolk sac and embryo proper of the mouse", Development, 126:5073-5084.
Palis et al., 2001, "Spatial and temporal emergence of high proliferative hematopoietic precursors during murine embryogenesis", Proc Natl Acad Sci, 98:4528-4533.

(Continued)

*Primary Examiner* — Blaine Lankford
(74) *Attorney, Agent, or Firm* — Riverside Law LLP

(57) ABSTRACT

The present invention provides a human cell population that can self-renew extensively and yet retain the capacity to differentiate into red blood cells (RBCs). These cells are referred to as extensively self-renewing erythroblasts (ESREs). The cells of the invention serve among other things as a renewable source of transfusable RBCs.

7 Claims, 23 Drawing Sheets

(56) References Cited

OTHER PUBLICATIONS

Migliaccio et al., 1986, "Human embryonic hemopoiesis. Kinetics of progenitors and precursors underlying the yolk sac—liver transition", J Clin Invest, 78:51-60.
Bertrand et al., 2007, "Definitive hematopoiesis initiates through a committed erythromyeloid progenitor in the zebrafish embryo", Development, 134:4147-4156.
Keller et al., 1993, "Hematopoietic commitment during embryonic stem cell differentiation in culture", Mol Cell Biol, 13:473-486.
Giarratana et al., 2011, "Proof of principle for transfusion of in vitro—generated red blood cells", Blood, 118(19): 5071-5079.
Levasseur et al., 2003, "Correction of a mouse model of sickle cell disease: lentiviral/antisickling β-globin gene transduction of unmobilized, purified hematopoietic stem cells", Blood, 102:4312-4319.
Bauer et al., 2012, "Reawakening fetal hemoglobin: prospects for new therapies for the β-globin disorders", Blood, 120:2945-2953.
Aladjem et al., 1998, "ES cells do not activate p53-dependent stress responses and undergo p53-independent apoptosis in response to DNA damage", Curr Biol, 8:145-155.
Bauer et al., 1999, "The glucocorticoid receptor is required for stress erythropoiesis", Genes Dev, 13: 2996-3002.
Carotta et al., 2004, "Directed differentiation and mass cultivation of pure erythroid progenitors from mouse embryonic stem cells", Blood, 104: 1873-1880.
Chang et al., 1993, "Inhibition of mouse GATA-1 function by the glucocorticoid receptor: possible mechanism of steroid inhibition of erythroleukemia cell differentiation", Mol Endocrinol, 7: 528-542.
Dolznig et al., 2001, "Establishment of normal, terminally differentiating mouse erythroid progenitors: molecular characterization by cDNA arrays", FASEB J, 14: 1442-1444.
Dolznig et al., 2006, "Erythroid progenitor renewal versus differentiation: genetic evidence for cell autonomous, essential functions of EpoR, Stat5 and the GR", Oncogene, 25: 2890-2900.
Ganguli et al., 2002, "The p53 tumour suppressor inhibits glucocorticoid-induced proliferation of erythroid progenitors", EMBO Rep, 3: 569-574.
Kingsley et al., 2004, "Yolk sac—derived primitive erythroblasts enucleate during mammalian embryogenesis", Blood, 104: 19-25.
Leberbauer et al., 2005, "Different steroids co-regulate long-term expansion versus terminal differentiation in primary human erythroid progenitors", Blood, 105: 85-94.
Lindemann, et al., 1969, "Pituitary Control of Erythropoiesis", Scand J Haematol, 6: 77-86.
Sengupta et al., 2001, "Ligand-dependent interaction of the glucocorticoid receptor with p53 enhances their degradation by Hdm2", Genes Dev, 15: 2367-2380.
Wessely et al., 1997, "The glucocorticoid receptor is a key regulator of the decision between self-renewal and differentiation in erythroid progenitors", EMBO J, 16: 267-280.
Bessis et al., 1978, "Erythropoiesis: comparison of in vivo and in vitro amplification", Blood Cells, 4:155-174.
Migliaccio et al., 2010, "Humanized Culture Medium for Clinical Expansion of Human Erythroblasts", Cell Transplant, 19: 453-469.
Miharada et al, 2006, "Efficient enucleation of erythroblasts differentiated in vitro from hematopoietic stem and progenitor cells", Nat Biotechnol, 24: 1255-1256.
Von Lindern et al., 2001, "Leukemic transformation of normal murine erythroid progenitors: v- and c-ErbB act through signaling pathways activated by the EpoR and c-Kit in stress erythropoiesis", Oncogene, 20: 3651-3664.
Waugh et al., 2013, "Development of membrane mechanical function during terminal stages of primitive erythropoiesis in mice", Exp, Hematol, 41(4): 398-408.
Zeuner, Ann et al., "Concice Review: Stem Cell-Derived Erythrocytes as Upcoming Players in Blood Transfusion", Stem Cells., vol. 30, No. 8, Jul. 24, 2012, pp. 1587-1596.
Gao, Rui et al., "Bmi1 Promotes Erythroid Development Through Regulating Ribosome Biogenesis", Stem Cells., vol. 33, No. 3, Nov. 11, 2014, pp. 925-938.

HUMAN EXTENSIVELY SELF-RENEWING ERYTHROBLASTS (ESRE)

CROSS-REFERENCE TO RELATED APPLICATIONS

This application is the U.S. national stage application filed under 35 U.S.C. § 371 claiming benefit to International Patent Application No. PCT/US14/038075, filed May 14, 2014, which is entitled to priority under 35 U.S.C. § 119(e) to U.S. Provisional Application No. 61/823,677, filed May 15, 2013, each of which is hereby incorporated by reference in its entirety.

STATEMENT REGARDING FEDERALLY SPONSORED RESEARCH OR DEVELOPMENT

This invention was made with government support under U01 HL099656 awarded by the National Institutes of Health (NIH). The government has certain rights in the invention.

BACKGROUND OF THE INVENTION

Over 16 million units of red blood cells (RBCs) are transfused yearly in the United States to meet the clinical need of critically ill patients following trauma, surgery, or cancer chemotherapy. Currently, the supply of RBCs for transfusion is solely dependent on donors, which is associated with infectious risk, high costs of screening, and supply bottlenecks, especially for rare blood types. Over the next several decades the needs for red cell transfusions will increase as the U.S. population ages. Therefore, alternative sources for blood transfusions are needed.

The generation of erythrocytes using embryonic stem (ES) cell-based approaches is limited by scalability and limited methodology for generating erythrocyte progenitors. Although previous technologies have used bone marrow-derived and cord blood-derived hematopoietic stem cells, usable production of erythroid progenitors has not been achieved. Conversely, technologies exist for terminal differentiation and enucleation of erythroid progenitors, however, production of ample amounts of the "starting cells" has not been successful (Giarratana, 2011). The present invention addresses this unmet need in the art.

SUMMARY OF THE INVENTION

The invention provides an isolated population of human extensively self-renewing erythroblasts (ESRE) that proliferates in culture and maintains the ability to terminally mature, wherein the ESRE is not immortalized.

In one embodiment, the population of ESRE is capable of undergoing at least 30 cell divisions.

In one embodiment, the population of ESRE is derived from a population of definitive erythroid progenitors further wherein the population of ESRE exhibits a higher expression level of Bmi-1 compared to erythroblasts undergoing restrictive self-renewal and primary proerythroblasts.

In one embodiment, the ESRE is genetically modified to express one or more therapeutic proteins.

In one embodiment, the ESRE is genetically modified to express a factor selected from the group consisting of factor IX, factor VIIIc, von Willebrand's factor, tissue plasminogen activator, protein C, protein S, antithrombin III, and any combination thereof.

The invention also provides a composition comprising an isolated population of human ESRE and an expansion medium comprising Epo, SCF, dexamethasone, and a lipid mixture.

In one embodiment, the expansion medium further comprises one or more of a Bmi-1 protein, a Bmi-1 peptide, and a Bmi-1 regulating agent.

The invention also provides an isolated population of human RBCs derived from a population of ESRE.

The invention also provides a method of generating a substantially pure population of ESRE from human cells. In one embodiment, the method comprises a) culturing human cells under conditions that promote generation of a population of differentiated cells, b) expanding the population of differentiated cells in an expansion medium comprising Epo, SCF, dexamethasone, and a lipid mixture, thereby generating a substantially pure population of ESRE.

In one embodiment, the human cells are selected from the group consisting of embryonic stem cells, induced-Pluripotent Stem (iPS) cells, adult stem cells, cord cells, bone marrow cells, and a combination thereof.

In one embodiment, the population of differentiated cells in step a) is derived from embryoid bodies (EB).

In one embodiment, in step a), the cells are cultured to produce a population of definitive erythroid progenitor cells.

In one embodiment, the cells are cultured in step a) for at least about 20 days.

In one embodiment, in step b), the population of ESRE undergo self-renewal cell divisions continuously for at least about 45 days.

In one embodiment, in step b), one or more of Bmi-1 protein, Bmi-1 peptide, and a Bmi-1 regulating agent is provided to the population of differentiated cells in an amount sufficient for regulating erythroid self-renewal.

In one embodiment, the Bmi-1 regulating agent is a hedgehog ligand.

In one embodiment, the expansion media is an animal component-free medium supplemented with about 2 U/mL Epo, about 100 ng/mL human recombinant SCF, about $10^{-6}$M dexamethasone, about 40 ng/mL human recombinant insulin-like growth factor-1, and about 0.4% lipid mixture.

The invention also provides a method of delivering a gene to a mammal. In one embodiment, the method comprises administering a gene delivery vehicle to the mammal wherein the vehicle comprises a genetically modified ESRE.

The invention also provides a method of generating a human red blood cell (RBC). In one embodiment, the method comprises culturing an ESRE in a differentiation medium comprising EPO and insulin.

The invention also provides a method of treating a subject having a need for a RBC transfusion. In one embodiment, the method comprises administering an isolated population of human RBCs derived from a population of ESRE to the subject.

In one embodiment, the RBC is generated from a cell obtained from the subject.

In one embodiment, the cell obtained from the subject is selected from the group consisting of an embryonic stem cell, an iPS cell, an adult stem cell, a cord blood cell, a bone marrow cell, and any combination thereof.

The invention also provides a method of treating a subject with a blood disorder. In one embodiment, the method comprises introducing into the subject a therapeutically effective amount of ESREs.

In one embodiment, the ESREs are genetically modified to express one or more factors so as to treat the subject with the blood disorder.

In one embodiment, the blood disorder is hemophilia.

In one embodiment, the factor is selected from the group consisting of factor VIII, or factor VIIIa, factor V, factor Va, factor IX, factor X, factor XI, factor XII, factor XIII, von Willebrand's factor, tissue plasminogen activator, protein C, protein S, antithrombin III, and any combination thereof.

The invention also provides a method of screening a test compound that modulates ESRE gene expression. In one embodiment, the method comprises contacting ESREs with a test compound and identifying the compound as a modulator of ESRE gene expression when gene expression level in the presence of the test compound is different than gene expression level in the absence of the test compound.

In one embodiment, the ESRE is genetically modified to comprise a nucleic acid sequence encoding a detectable polypeptide operably linked to a globin gene promoter.

In one embodiment, the globin gene promoter is selected from the group consisting of human gamma-globin gene promoter and human beta-globin gene promoter.

In one embodiment, the detectable polypeptide is selected from the group consisting luciferase, fluorescent protein, red fluorescent protein, phosphatase, peroxidase, kinase, chloramphenicol transferase, and beta-galactosidase.

In one embodiment, the method comprises measuring detectable polypeptide levels in the presence and absence of the test compound, wherein an increase in the detectable polypeptide level in the presence of the test compound compared to the detectable polypeptide level in the absence of the test compound identifies the test compound as a compound that activates the globin gene promoter.

In one embodiment, the method comprises measuring detectable polypeptide levels in the presence and absence of the test compound, wherein a decrease in detectable polypeptide levels in the presence of the test compound compared to detectable polypeptide levels in the absence of the test compound identifies the test compound as a compound that inhibits expression of the globin gene.

In one embodiment, the test compound is selected from the group consisting of a small molecule, a nucleic acid molecule, a polypeptide, a synthetic compound, and a naturally-occurring compound.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A and 1B, is a series of images showing mammalian erythropoiesis. (FIG. 1A) Steady-state erythropoiesis in vivo is characterized by limited expansion of erythroid-committed progenitors (BFU-E, CFU-E) and erythroid precursors (ProE, BasoE, PolyE and OrthoE) that enucleate to form reticulocytes (retics). (FIG. 1B) The ex vivo culture of cord blood and adult marrow gives rise to erythroblasts with restricted self-renewal capacity.

FIGS. 2A and 2B, is a series of images showing murine extensively self-renewing erythroblasts (ESREs). (FIG. 2A) Erythroblast cultures from adult marrow display restricted self-renewal. In contrast, erythroblast cultures from E9.5 mouse yolk sac and E14.5 liver undergo extensive self-renewal. (FIG. 2B) Proliferating erythroblasts express high levels of c-Kit and have a proerythroblast morphology. Upon differentiation, TER119 expression increases and the cells mature into reticulocytes.

FIG. 4, comprising (FIG. 4A) Two sequential waves of erythroid progenitors emerge from human EBs. (FIG. 4B) Morphology (upper) and cellular composition (lower) of erythroid colonies reveal morphologies consistent with primitive and definitive erythroid identities. (FIG. 4C) Gene expression analysis of 5 erythroid colonies from day 11-19 EBs (EBD11, EBD19). Erythroid colonies from day 11 to day 16 EBs express predominantly the embryonic ε-globin gene (upper panel) but not glucocorticoid receptor (GR, the Nr3c1 gene; lower panel). In contrast, erythroid colonies from day 17 and day 19 EBs express predominantly the fetal γ-globin gene (upper panel) as well as GR (lower panel). (FIG. 4D) Upper panel: Self-renewing human erythroblasts derived from H1 human ES cells differentiated in vitro for 19 days. Lower panel: human erythroblasts differentiated in EPO and insulin mature into reticulocytes in vitro. (FIG. 4E) Scheme for the serum-free differentiation of human ESCs as embryoid bodies (EBs) to blood cell fates. FIGS. 4F through 4H are images of human definitive self-renewing erythroblasts. (FIG. 4F) Human self-renewing erythroblasts (SR) express the erythroid-specific marker CD235a and contain a large nucleus (DAPI). In vitro differentiation of these cells (Diff) results in small RBCs lacking DNA. (FIG. 4G) Relative levels of β-like globin mRNAs expressed by self-renewing (SR) and differentiated (Diff) hESC-derived erythroid cells. Human erythroblast maturation is associated with a globin "switch" from fetal γ-globin to adult β-globin. (FIG. 4H) Mouse ESREs (GFP-labeled) are able to fully mature in vivo and to circulate as RBCs in vivo for several weeks. (FIG. 4I) Morphology of the proliferation of erythroblasts (at day 36 of expansion) is depicted.

FIGS. 5A through 5C, is a series of images demonstrating p53 biology in restricted versus extensive erythroid self-renewal. (FIG. 5A) Response to mitomycin C of erythroblasts undergoing either restricted or extensive self-renewal. (FIG. 5B) Imaging flow cytometry of non-apoptotic and apoptotic self-renewing erythroblasts exposed to 0.1 uM mitomycin C. Apoptotic cells have nuclear blebbing. (FIG. 5C) Expression (qPCR) of p53-responsive genes in erythroblasts treated with mitomycin C or vehicle. The apoptosis effector PERP is not expressed by ESREs. nd=not detected.

FIG. 13, comprising FIG. 13A shows that adult bone marrow cells (derived from wild-type adult mice) infected with Bmi-1 overexpression have continued to proliferate for at least twice as long compared to empty vector control. FIG. 13B shows that mouse adult bone marrow cells (derived from Protein 4.1 knockout mouse) infected with Bmi-1 overexpression have continued to proliferate at least more than 30 days compared to empty vector control.

FIG. 16, comprising FIG. 16A is a schematic of two ways to generate ESREs whereby 1) ESREs can be derived from expanding the definitive embryonic hematopoietic progenitors cell population or 2) transduction of Bmi1 into fetal/adult hematopoietic progenitors and expanding this cell population. FIG. 16B is a schematic showing that going from pluripotent state of human embryonic stem cells to enucleated red blood cells involves a series of different steps. First, human ESCs are differentiated toward "definitive erythroid progenitors." When definitive potentials are found, then those erythroid cells are further cultured with EPO, SCF, and DEX to induce self-renewal of erythroblasts. In addition, these self-renewing erythroblasts maintain their functional ability to terminally mature. FIG. 16C is a schematic showing definitive erythroid progenitors from adult bone marrow are transduced with Bmi1 overexpression, then, those erythroid cells with Bmi1 overexpression are continued to culture with EPO, SCF, and DEX to induce extensive self-renewal of erythroblasts. In addition, these self-renewing erythroblasts with Bmi1 overexpression maintain their functional ability to terminally mature.

DETAILED DESCRIPTION

Figure 1:
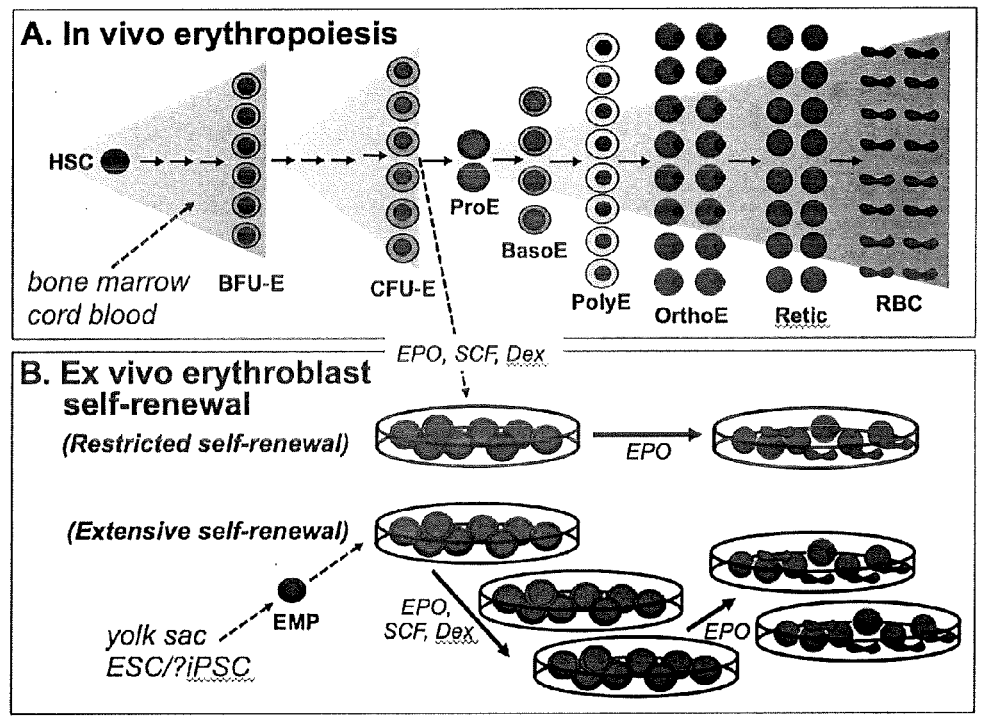
FIG. 1, comprising

The invention relates to the discovery of the generation of a human cell population that can self-renew extensively and yet retain the capacity to differentiate into red blood cells (RBCs). These cells are referred herein as extensively self-renewing erythroblasts (ESREs). The cells of the invention serve among other things as a renewable source of RBCs.

In one embodiment, ESREs of the invention are generated from differentiating a stem cell using a differentiation protocol that leads to the emergence of definitive erythroid progenitor potential. In one embodiment, the method comprises culturing a stem cell in a condition that generates erythroid progenitor potential from which ESREs can be generated in vitro. In one embodiment, ESREs are generated by placing the differentiated stem cells into an expansion media. In one embodiment, the expansion media comprises a serum free medium supplemented with Epo, SCF, dexamethasone, insulin-like growth factor-1, and a lipid mixture. In one embodiment, the culture of differentiated stem cells in an expansion media of the invention results in the outgrowth of erythroid precursors that continue to proliferate without differentiating, that is, they undergo self-renewal divisions. In one embodiment, these self-renewing erythroblasts continue to self-renew continuously for at least 45 days. In one embodiment, ESREs are not immortalized. The ESREs of the invention can then be differentiated into RBCs. In one embodiment, placement of ESRE in a differentiation media results in their maturation into late-stage erythroblasts and reticulocytes. In one embodiment, the ESREs differentiate when injected in vivo.

In one embodiment, the generation and maintenance of ESREs of the invention is improved by providing the cells with an agent that activates Bmi-1 in the cell. This is because the invention is partly based on the discovery that Bmi-1 is a central regulator of erythroid self-renewal. That is, it was observed that ESREs exhibit a higher expression level of Bmi-1 compared to erythroblasts undergoing restricted (SRE) self-renewal, as well as multiple populations of primary proerythroblasts (ProE). In addition, it was observed that cells overexpressing Bmi-1 continued to proliferate for more than 75 days. Accordingly, in one embodiment, the invention includes a method for regulating erythroid self-renewal. In one embodiment, the method comprises providing a cell having erythroid progenitor potential, Bmi-1 or a variant or fragment thereof and/or a Bmi-1 regulating agent in an amount sufficient for regulating erythroid self-renewal of the cell; and culturing the cell for a time sufficient for the regulating erythroid self-renewal. In one embodiment, regulating erythroid self-renewal of the cell is the promotion of the expansion of the cells.

In one embodiment of this invention, the Bmi-1 or a variant or fragment thereof and/or the Bmi-1 regulating agent are selected from the group consisting of a small molecule, a lipid molecule, a sugar, and a complex thereof.

In another embodiment, the Bmi-1 regulating agent includes but is not limited to a lipid, a lipoprotein, cholesterol, a phospholipid and a fatty acid. In one embodiment, a mixture of a lipid, a lipoprotein, cholesterol, a phospholipid, and a fatty acid is a source of lipids that can be supplemented to the cell culture to regulate erythroid self-renewal. In one embodiment, the Bmi-1 regulating agent is hedgehog ligand. In another embodiment, the Bmi-1 regulating agent is 25-hydroxycholesterol.

In one embodiment, activation of Bmi-1 can be used to generate ESREs from cord blood cells or bone marrow cells.

In another embodiment, the invention provides a method for screening for an agent that regulates erythroid self-renewal. The method comprises the steps of: (i) providing a candidate substance for the agent; (ii) exposing a cell containing Bmi-1 to the substances; and (iii) determining whether or not the Bmi-1 is regulated, wherein when the Bmi-1 is regulated, the substance is determined to be an agent capable of regulating erythroid self-renewal.

The invention also includes the progeny of ESREs, including any cell type generated during the differentiation of ESREs towards red blood cells (RBCs) or cells that exhibit at least one characteristic of a RBC. In one embodiment, the invention includes a method of making an ESRE and a progeny cell therefrom. In another embodiment, the invention includes a culture system for deriving an ESRE as well as progenies of ESREs. In various embodiments, the invention includes a method of using ESREs and progenies therefrom to treat a subject in need of RBCs. In one embodiment, the ESREs of the invention allows for the production of RBCs. The cells of the invention provide a limitless source of RBCs.

In one embodiment, the invention provides compositions and methods for generating or creating enhanced numbers of erythroid progenitor cells from stem cells, or equivalent cells. In one embodiment, the invention provides a new methodology for making RBCs. In another embodiment, the invention teaches methods of increasing propensity of committed stem cell differentiation towards the erythroid lineage.

In one embodiment, the invention provides compositions, products (articles) of manufacture, and/or isolates, mixtures or cultures of cells comprising embryoid bodies (EBs) or stem cells, including progenies thereof; a sufficient amount of a growth factor; a composition or agent for stimulating an erythroid lineage commitment or an equivalent thereof, to induce formation (or differentiation to) ESREs.

The invention provides uses of the compositions, products of manufacture, or isolates, mixtures or cultures of cells of the invention, to make ESREs.

In one embodiment, the ESREs of the invention can be used to study the biology of diseases intrinsic to red blood cells, including red cell membrane disorders, disorders of globin gene expression, and disorders of red cell maturation.

In one embodiment, the ESREs of the invention can be used as a vehicle to express a desired gene and/or protein. For example, RBCs derived from the ESREs of the invention can be used as a vehicle to express a desired gene and/or protein. The desired gene can be genetically modified at the stem cell stage (e.g., prior to arriving at the ESREs of the invention). Alternatively, the ESREs of the invention can be genetically modified at the self-renewal stage to express the desired gene.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

As used herein, the term "basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of base media are known in the art of mammalian cell culture, such as Dulbecco's Modified Eagle Media (DMEM), Knockout-DMEM (KO-DMEM), and DMEM/F12, although any base medium that supports the growth of primate embryonic stem cells in a substantially undifferentiated state can be employed.

The term "Bmi-1" refers to a component of the Polycomb group multiprotein PRC-1 like complex, a complex class required to maintain the transcriptionally repressive state of many genes throughout development. Bmi-1 is required for the maintenance of adult self-renewing hematopoietic stem cells (Park et al., 2003 Nature 423:302-305).

As intended herein the expression "cell culture medium" relates to any medium, in particular any liquid medium, liable to sustain the growth of eukaryotic cells, in particular mammalian cells, more particularly human cells.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

As intended herein the expression "cells of the hematopoietic lineage" relates to cells to be found in the blood of mammals, in particular of humans, and to cells liable to yield such blood cells upon differentiation. More particularly, the expression "cells of the hematopoietic lineage" according to the invention relates to cells of the erythrocytic lineage, that is red blood cells (also called erythrocytes) and cells which are liable to yield red blood cells upon differentiation, either directly, i.e. in one step, or indirectly, i.e. in several steps. As is well-known to one of skill in the art, cells of the erythrocytic lineage notably comprise, classified by increasing degree of differentiation, embryonic stem cells, hematopoietic stem cells (HSCs), pro-erythroblasts, erythroblasts, reticulocytes, enucleated cells, in particular enucleated reticulocytes, and red blood cells. Cells of the hematopoietic lineage according to the invention thus notably encompass stem cells, in particular embryonic stem cells (ESC), adult stem cells, such as hematopoietic stem cells (HSCs), induced-pluripotent stem (iPS) cells, as well as embryoid bodies, but also pro-erythroblasts, erythroblasts, reticulocytes, and enucleated cells, in particular enucleated reticulocytes. Preferably, the cells of the hematopoietic lineage of the invention are human cells.

As used herein, the term "clotting factor," refers to molecules, or analogs thereof which prevent or decrease the duration of a bleeding episode in a subject.

The term "comparator control,", as used herein, relates to a level of expression or activity which may be determined at the same time as the test sample by using a sample previously collected and stored from a subject whose disease state, e.g. cancerous, non-cancerous, is/are known.

The term "differentiated cell" refers to a cell of a more specialized cell type derived from a cell of a less specialized cell type (e.g., a stem cell or ESRE) in a cellular differentiation process.

"Differentiation medium" is used herein to refer to a cell growth medium comprising an additive or a lack of an additive such that a stem cell, ESRE or other such progenitor cell, that is not fully differentiated, develops into a cell with some or all of the characteristics of a differentiated cell when incubated in the medium.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "erythroid progenitor cell" as used herein refers to a red blood cell precursor cell that is capable of differentiating to a red blood cell.

The term "extensively expanded" as used herein refers to cell populations which have undergone at least about 30 or more cell population doublings and wherein the cells are non-senescent, are not immortalized, and continue to maintain the normal karyotype found in the cell species of origin.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

As intended herein, the term "growth" relates to the multiplication of cultured cells. As intended herein, the term "differentiation" relates to the acquisition by cells cultured in a culture medium of cellular characteristics which are not present in the cells initially used for seeding the cell culture medium. As intended herein "differentiation" notably denotes the acquisition of characteristics further committing the cells in the pathway towards differentiation into red blood cells. Thus, the cell culture medium of the invention is particularly useful for growing undifferentiated cells, such as embryonic stem cells, adult stem cells, such as hematopoietic stem cells, induced-pluripotent stem cells (iPS), or embryoid bodies, and differentiating them into reticulocytes, enucleated cells or red blood cells.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency), Von Willebrand disease, factor Xi deficiency (PTA deficiency), Factor XII deficiency, deficiencies or structural abnormalities in fibrinogen, prothrombin, Factor V, Factor VII, Factor X or factor XIII, Bernard-Soulier syndrome is a defect or deficiency in GPIb. GPIb, the receptor for vWF, can be defective and lead, to lack of primary clot formation (primary hemostasis) and increased bleeding tendency), and thrombasthenia of Glanzman and Naegeii (Glanzmann thrombasthenia). In liver failure (acute and chronic forms), there is insufficient production of coagulation factors by the liver; this may increase bleeding risk.

An "isolated cell" refers to a cell which has been separated from other components and/or cells which naturally accompany the isolated cell in a tissue or mammal.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, a "substantially purified" cell is a cell that is essentially free of other cell types. Thus, a substantially purified cell refers to a cell which has been purified from other cell types with which it is normally associated in its naturally-occurring state.

As used herein, the term "substantial capacity for self-renewal" means having the ability to go through numerous cycles of cell division resulting in the production of multiple generations of cell progeny (thus, with each cell division, one cell produces two "daughter cells" wherein at least one daughter cell is capable of further cell division). One measure of "substantial capacity for self-renewal" is indicated by the ability of a cell population to undergo at least about 10, 15, 20, 25, 30, 35, 40, 45, 50 or more cell doublings.

Another measure of "substantial capacity for self-renewal" is indicated by maintenance of the ability of a cell population to re-populate, or approach confluence in, a tissue culture vessel after cell culture passaging (when the same or similar culture conditions are maintained). Thus, an example of "substantial capacity for self-renewal" is demonstrated when a cell population continues to re-populate a tissue culture dish in a period of time of at least about 25%, 50%, 60%, 70%, 80%, 90%, 95% or 100% of the time required for such re-population during early cell culture doublings (such as before a cell population has undergone more than about 10 population doublings). Another measure of "substantial capacity for self-renewal" is maintenance of a consistent rate of population doubling time or of a consistent and relatively rapid rate of population doubling.

"Test agents" or otherwise "test compounds" as used herein refers to an agent or compound that is to be screened in one or more of the assays described herein. Test agents include compounds of a variety of general types including, but not limited to, small organic molecules, known pharmaceuticals, polypeptides; carbohydrates such as oligosaccharides and polysaccharides; polynucleotides; lipids or phospholipids; fatty acids; steroids; or amino acid analogs. Test agents can be obtained from libraries, such as natural product libraries and combinatorial libraries. In addition, methods of automating assays are known that permit screening of several thousands of compounds in a short period.

A "therapeutic" treatment is a treatment administered to a subject who exhibits a sign or symptom of pathology, for the purpose of diminishing or eliminating those signs or symptoms.

As used herein, "treating a disease or disorder" means reducing the frequency or severity with which a sign or symptom of the disease or disorder is experienced by a patient.

The phrase "therapeutically effective amount," as used herein, refers to an amount that is sufficient or effective to prevent or treat (delay or prevent the onset of, prevent the progression of, inhibit, decrease or reverse) a disease or disorder.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention relates to the discovery of the generation of a human cell population that can self-renew extensively and yet retain the capacity to differentiate into red blood cells (RBCs). These cells are referred herein as extensively self-renewing erythroblasts (ESREs). The cells of the invention serve among other things as a renewable source of transfusable RBCs.

In one embodiment, ESREs of the invention are cells that represent primary erythroblasts, but possess limitless proliferation potential while maintaining the ability to produce enucleated RBCs. Therefore ESREs serve as a source for producing blood.

In one embodiment, ESREs of the invention are generated from differentiating a stem cell using a differentiation protocol that leads to the emergence of definitive erythroid progenitor potential. An example of a stem cell includes but is not limited to embryonic stem cell, adult stem cell, iPS cells, and the like. Additional non-limiting examples of exemplary stem cells include different adult or embryonic stem cells; totipotent, pluripotent or multipotent stem cell or progenitor or precursor cells; cord blood stem cells; placental stem cells; bone marrow stem cells; amniotic fluid stem cells; neuronal stem cells; circulating peripheral blood stem cells; mesenchymal stem cells; germinal stem cells; adipose tissue derived stem cells; exfoliated teeth derived stem cells; hair follicle stem cells; dermal stem cells; parthenogenically derived stem cells; reprogrammed stem cells; and side population stem cells.

In certain embodiments, the stem cell used in the present invention is pluripotent. In one embodiment, the pluripotent stem cell is an embryonic stem cell or embryo-derived cell. In certain embodiments, the pluripotent stem cell is an induced pluripotent stem cell. In certain embodiments, the pluripotent stem cell is an adult stem cell. In certain embodiments, the pluripotent stem cell is a human cell. In certain embodiments, the pluripotent stem cell is genetically manipulated prior to differentiation.

In one embodiment, differentiating a stem cell into an ESRE of the invention comprises culturing the stem cell in conditions that induce formation of embryoid bodies (EB) and differentiation towards hematopoietic lineages. In one embodiment, the differentiation of a stem cell comprises sequential application of growth factors to generate a desired hematopoietic fate.

There is a critical need for available blood for transfusion. The present invention provides methods and compositions for generating human ESREs to serve as a renewable source for RBCs. In one embodiment, the RBCs derived from the ESREs of the invention are a source of transfusable RBCs. Therefore in one embodiment, the cells of the invention are useful in blood banking and transfusion. The cells and methods of the present invention also provide a safe and reliable advance beyond the traditional reliance on blood donations, and help prevent critical shortages in available blood.

The invention is based on the discovery that it is necessary to differentiate the stem cells past a primitive erythroid fate to a definitive erythroid fate in order to generate the cells of the invention.

In one embodiment, the method comprises culturing a stem cell in a condition that generates erythroid progenitor potential from which ESREs can be generated in vitro. These ESREs can then be differentiated into a desirable differentiated cell, for example RBCs.

In one embodiment, ESREs are generated by culturing a starting cell population under conditions that promote differentiation of the starting cell population into ESREs of the invention. In one embodiment, the starting cell source can be any type of stem cell. In one embodiment, the stem cell is a human pluripotent stem cell.

In one embodiment, differentiating the human pluripotent stem cell into the ESRE of the invention is accomplished in vitro by a method comprising sequential application of growth factors to generate a hematopoietic fate. Also the media contains 1% penicillin/streptomycin (Invitrogen) to help prevent bacterial contamination. In one embodiment, the first stage of culturing comprises culturing a cell culture comprising a human pluripotent stem cell in serum-free media in the presence of at least two growth factors, wherein the growth factors are in an amount sufficient to induce the differentiation of the human pluripotent stem cell into embryoid bodies. In one embodiment, the growth factors are present at a sufficient amount of time to induce the differentiation of the human pluripotent stem cell into embryoid bodies. In one embodiment, the at least two growth factor includes BMP4 and VEGF. Thus, the present invention relates to a cell culture medium for the growth and/or differentiation of cells of the hematopoietic lineage, comprising: BMP4 at a concentration of about 25 ng/mL; VEGF at a concentration of about 50 ng/mL. In one embodiment, the first stage of culturing comprises culturing the cells for about 2 days (48 hours). In another embodiment, BMP4 is at a concentration range of about 10 ng/mL to about 50 ng/mL; VEGF is at a concentration range of about 25 ng/mL to about 100 ng/mL.

In one embodiment, the second stage of culturing comprises culturing a cell culture comprising cells from the first stage of culturing in serum-free media in the presence of at least three growth factors, wherein the growth factors are in an amount sufficient to induce the differentiation of the cells from the first stage of differentiation along the mesodermal differentiation path. In one embodiment, the growth factors are present at a sufficient amount of time to induce the differentiation of the cells from the first stage of culturing along the mesodermal differentiation path. In one embodiment, the at least three growth factor includes BMP4, VEGF, bFGF, and Flt3L. Thus, the present invention relates to a cell culture medium for the growth and/or differentiation of cells of the hematopoietic lineage, comprising: BMP4 at a concentration of about 25 ng/mL; VEGF at a concentration of about 50 ng/mL; bFGF at a concentration of about 20 ng/mL; Flt3L at a concentration of about 10 ng/mL. In another embodiment, BMP4 is at a concentration range of about 10 ng/mL to about 50 ng/mL; VEGF is at a concentration range of about 25 ng/mL to about 100 ng/mL; bFGF is at a concentration range of about 5 ng/mL to about 50 ng; Flt3L is at a concentration range of about 2 ng/mL to about 30 ng/mL. Also the media can contain 1% penicillin/streptomycin (Invitrogen) to help prevent bacterial contamination. In one embodiment, the second stage of culturing comprises culturing the cells for 2 days (48 hours).

In one embodiment, the third stage of culturing comprises culturing a cell culture comprising cells from the second stage of culturing in serum-free media in the presence of at least four growth factors, wherein the growth factors are in an amount sufficient to induce the differentiation of the cells from the second stage of differentiation along the hematopoietic differentiation path. In one embodiment, the growth factors are present at a sufficient amount of time to induce the differentiation of the cells from the second stage of culturing along the hematopoietic differentiation path. In one embodiment, the at least four growth factor includes bFGF, VEGF, Flt3L, and SCF. Thus, the present invention relates to a cell culture medium for the growth and/or differentiation of cells of the hematopoietic lineage, comprising: bFGF at a concentration of about 20 ng/mL; VEGF at a concentration of about 50 ng/mL; Flt3L at a concentration of about 10 ng/mL; SCF at a concentration of about 50 ng/mL. In another embodiment, bFGF is at a concentration range of about 5 ng/mL to about 50 ng; VEGF is at a concentration range of about 25 ng/mL to about 100 ng/mL; Flt3L is at a concentration range of about 2 ng/mL to about 30 ng/mL; SCF at a concentration range of about 25 ng/mL to about 100 ng/mL. Also the media contains 1% penicillin/streptomycin (Invitrogen) to help prevent bacterial contamination. In one embodiment, the third stage of culturing comprises culturing the cells for 2 days (48 hours).

In one embodiment, the fourth stage of ES cell differentiation comprises culturing in serum-free media in the presence of at least seven growth factors, wherein the growth factors are in an amount sufficient to induce the differentiation of the cells from the third stage of culturing further along the hematopoietic differentiation path. In one embodiment, the growth factors are present at a sufficient amount of time to induce the differentiation of the cells from the third stage of culturing further along the hematopoietic differentiation path. In one embodiment, the at least seven growth factor includes VEGF, SCF, IL6, TPO, IL11, IGF1, and EPO. Thus, the present invention relates to a cell culture medium for the growth and/or differentiation of cells of the hematopoietic lineage, comprising: VEGF at a concentration of about 50 ng/mL; SCF at a concentration of about 50 ng/mL; IL6 at a concentration of about 10 ng/mL; TPO at a concentration of about 100 ng/mL; IL11 at a concentration of about 5 ng/mL; IGF1 at a concentration of about 25 ng/mL; EPO at a concentration of about 0.05 U/mL. In one embodiment, VEGF is at a concentration range of about 25 ng/mL to about 100 ng/mL; SCF is at a concentration range of about 25 ng/mL to about 100 ng/mL; IL6 is at a concentration range of about 2 ng/mL to 50 ng/mL; TPO is at a concentration range of about 50 ng/mL to about 200 ng/mL; IL11 is at a concentration range of about 2 ng/mL to 20 ng/mL; IGF1 is at a concentration range of about 10 ng/mL to about 50 ng/mL; EPO is at a concentration of about 0.01 U/mL to about 0.2 U/mL. Also the media contains 1% penicillin/streptomycin (Invitrogen) to avoid contamination. In one embodiment, the fourth stage of culturing comprises culturing the cells for 2 days (48 hours).

In one embodiment, the fifth stage of culturing comprises culturing a cell culture comprising cells from the fourth stage of culturing in serum-free media in the presence of at least three growth factors, wherein the growth factors are in an amount sufficient to induce the differentiation of the cells from the fourth stage of culturing along the hematopoietic maturation path. In one embodiment, the growth factors are present at a sufficient amount of time to induce the differentiation of the cells from the fourth stage of culturing along the hematopoietic maturation path. In one embodiment, the at least three growth factor includes SCF, IGF1, and EPO. Thus, the present invention relates to a cell culture medium for the growth and/or differentiation of cells of the hematopoietic lineage, comprising: SCF at a concentration of about 100 ng/mL; IGF1 at a concentration of about 25 ng/mL; EPO at a concentration of about 2 U/mL. In one embodiment, SCF is at a concentration range of about 50 ng/mL to about 200 ng/mL; IGF1 is at a concentration range of about 10 ng/mL to about 50 ng/mL; EPO is at a concentration range of about 0.05 U/mL to about 5 U/mL. In one embodiment, the fifth stage of culturing comprises culturing the cells from day 8 to day 38.

In one embodiment, the invention provides a differentiation protocol as set forth in Table 1.

TABLE 1

Differentiation of human ES cells by sequential application of growth factors to generate hematopoietic fates

| | Day | | | | |
|---|---|---|---|---|---|
| | 0 | 2 | 4 | 6 | 8 to 38 |
| Growth Factors | BMP4, VEGF | BMP4, VEGF bFGF Flt3L | bFGF, VEGF, Flt3L SCF | VEGF, SCF, IL6, TPO, IL11, IGF1, EPO | SCF, IGF1, EPO |

TABLE 1-continued

Differentiation of human ES cells by sequential application of growth factors to generate hematopoietic fates

| Day | | | | |
|---|---|---|---|---|
| 0 | 2 | 4 | 6 | 8 to 38 |
| Maturation | Mesoderm formation | Endothelium-> Hemogenic Endothelium--> Hematopoietic Induction | | Hematopoietic maturation |

However, the invention should not be limited to the differentiation of human ES cells as set forth in Table 1. Rather, the invention includes alternative approaches to the differentiation of human ES cells to mesoderm/blood fates where by ESRE of the invention can be obtained. This is because the invention is partly based on the discovery that definitive erythroid progenitors emerging from hESCs can be distinguished from primitive erythroid progenitors by differential gene expression and cell morphology.

Exemplary alternative approaches for differentiating human ES cells to mesoderm/blood fates include but are not limited to: coculturing ES cells with fetal human liver clone B (FH-B-hTERT) cells, increasing expression of HoxB4 in ES cells, inhibiting the Wnt signaling pathway using antagonists such as DKKs during ES cell differentiation, and coculturing ES cells with the macrophage colony-stimulating factor (M-CSF)-deficient stromal cell line OP9. See Olivier et al., 2006, Exp. Hematol. 1635-1642, Kyba et al., 2002, Cell 109:29-37, Paluru et al., 2014, Stem Cell Res. 12:441-451, and Vodyanik et al., 2005, Blood 105:617-626, each of which is herein incorporated by reference in its entirety.

Generation of ESREs

In one embodiment, ESREs are derived from the definitive erythroid progenitor cell population arising from the ES cell differentiation protocol discussed elsewhere herein. In one embodiment, the definitive erythroid progenitor cell population arises between about 17-40 days of ES cell differentiation from the protocol of Table 1. These definitive erythroid progenitors can be recognized by performing colony assays in methylcellulose supplemented with EPO (10 U/ml) and SCF (100 ng/ml).

In one embodiment, ESREs are generated by placing the differentiated ES cells into an expansion media. In one embodiment, the expansion media comprises StemSpan™-ACF (Stem Cell Technologies) supplemented with 2 U/mL human recombinant Epo (Amgen), 100 ng/mL human recombinant SCF (PeproTech), $10^{-6}$M dexamethasone (Sigma), 40 ng/mL human recombinant insulin-like growth factor-1 (PeproTech), 0.4% lipid mixture EX-CYTE (Millipore), and 1% penicillin/streptomycin (Invitrogen). In one embodiment, the human ES cells are differentiated for about 17-40 days to contain definitive erythroid potential from which ESREs can be generated by in vitro culture. In one embodiment, the culture of differentiated ES cells in an expansion media of the invention results in the outgrowth of erythroid precursors that continue to proliferate without differentiating, that is, they undergo self-renewal divisions. In one embodiment, these self-renewing erythroblasts continue to self-renew continuously for at least 45 days.

In one embodiment, the expansion of the desired cell population (e.g., self-renewing erythroblasts) can be regulated by regulating Bmi-1 in the cell. This is because the invention is partly based on the discovery that Bmi-1 is a central regulator of erythroid self-renewal. Accordingly, the invention provides a method for regulating erythroid self-renewal. In one embodiment, the method comprises the steps of: (i) providing to the self-renewing erythroblasts, Bmi-1 or a variant or fragment thereof and/or a Bmi-1 regulating agent in an amount sufficient for regulation of the expansion of the self-renewing erythroblasts; and (ii) culturing the self-renewing erythroblasts for a time sufficient for regulation of the expansion. A technique for providing Bmi-1 or a variant or fragment thereof and/or a Bmi-1 regulating agent to a self-renewing erythroblast is well known in the art. For example, the technique comprises culturing a cell in a medium and providing the agent to the medium. The present invention is not limited to this. An amount sufficient for regulation of the expansion can be appropriately determined by those skilled in the art. Self-renewing erythroblasts can be cultured using common techniques well known in the art. A time sufficient for regulation of the expansion can be appropriately determined by those skilled in the art in view of the present specification.

Therefore, according to another aspect of the present invention, a composition for regulating the expansion of self-renewing erythroblasts is provided, which comprises Bmi-1 or a variant or fragment thereof and/or a Bmi-1 regulating agent in an amount sufficient for regulation of the expansion.

Preferably, the present invention provides a composition and method for promoting the expansion of self-renewing erythroblasts. The present invention provides a remarkable effect in the art. As used herein, the term "promotion of expansion" refers to promotion of the self-replication of a self-renewing erythroblast. The term "promotion of expansion" in relation to a cell population refers to the proportion of self-renewing erythroblasts maintaining the undifferentiated state is increased in the cell population. By observing cells, it can be determined whether or not promotion of expansion occurs.

Bmi-1 or a variant or fragment thereof and/or a Bmi-1 regulating agent for use in the present invention may be exogenous or endogenous. Preferably, the agent is exogenous. In the present invention, an exogenous Bmi-1 or its equivalent is provided to a cell, thereby making it possible to regulate (particularly, promote) the expansion of the cell. This effect could not be conventionally predicted. Bmi-1 or a variant or fragment thereof and/or a Bmi-1 regulating agent of the present invention may be endogenous. In this case, an endogenous Bmi-1 may be supplemented with an exogenous agent to enhance the effect thereof.

Bmi-1 or a variant or fragment thereof and/or a Bmi-1 regulating agent for use in the present invention may be in the form of a nucleic acid or a protein, or other forms (e.g., a small molecule, a lipid molecule, a sugar, or a complex thereof).

In another embodiment, the Bmi-1 regulating agent of the present invention includes Bmi-1 activating agent. Such an activating agent can be obtained by screening substance libraries using techniques well known in the art. Examples of such a Bmi-1 activating agent include, but are not limited to, a molecule capable of controlling the phosphorylated state of Bmi-1, a molecule capable of controlling the expression of Bmi-1 at the transcription level, and the like.

In one embodiment, the generation and maintenance of ESREs of the invention is improved by providing the cells with an agent that activates Bmi-1 in the cell. In one embodiment, activating Bmi-1 in the self-renewing erythroblasts allows the cells to continue to proliferate for more than 75 days.

However, the invention should not be limited to activating Bmi-1 to promote self-renewing and/or promote self replication of a self-renewing erythroblast. Rather, the invention includes regulating hedgehog to promote self-renewing and/or promote self replication of a self-renewing erythroblast.

Hedgehog ligands are able to regulate hedgehog by inducing a signal in the hedgehog pathway, and may be useful within the compositions and methods of the present invention. Non-limiting examples of Hedgehog ligands include Sonic hedgehog (Shh), Desert hedgehog (Dhh), Indian hedgehog (Ihh), tiggie-winkle hedgehog (Thh), purmorphamine, and oxysterols. Oxysterols are naturally occurring molecules derived from the enzymatic and nonenzymatic oxidation of cholesterol. Examples of oxysterols include, but are not limited to, 20(S)-hydroxycholesterol (20(S)—OHC), 7β-hydroxycholesterol (7β-OHC), 19-hydroxycholesterol (19-OHC), 22(R)-hydroxycholesterol (22(R)—OHC), 22(S)-hydroxycholesterol (22(S)—OHC), 24-hydroxycholesterol (24-OHC), 25-hydroxycholesterol, (25-OHC), 26-hydroxycholesterol (26-OHC). natural 20(S)-hydroxycholesterol (nat-20(S)—OHC), natural 20(R)-hydroxycholesterol (nat-20(R)—OHC), natural 20(S)-hydroxycholesterol with a terminal alkyne group (nat-20(S)-yne), and the enantiomer of natural 20(S)-hydroxycholesterol (ent-20 (S)—OHC). See Moon et al., 2011, Cell Res. 21:1305-1315, Nachtergaele et al., 2012, Nat. Chem. Biol. 8:211-220, and Wang et al., 2012, Oncogene 31:187-199, each of which is herein incorporated by reference in its entirety.

Further, one of skill in the art would, when equipped with this disclosure and the methods exemplified herein, appreciate that a Hedgehog ligand includes such ligands as discovered in the future, as can be identified by well-known criteria in the art of biochemistry and cell biology. Therefore, the present invention is not limited in any way to any particular Hedgehog ligand activator as exemplified or disclosed herein; rather, the invention encompasses those activators that would be understood by the routineer to be useful as are known in the art and as are discovered in the future.

Accordingly, one aspect of the invention provides a method of activating Bmi-1 in a cord blood cell or a bone marrow cell to generate a self-renewing and/or promote self replication of a self-renewing erythroblast. In another aspect, the invention provides a method of regulating hedgehog in a cord blood cell or a bone marrow cell to generate a self-renewing and/or promote self replication of a self-renewing erythroblast.

Generating RBCs from ESREs

In one embodiment, placement of ESRE in a differentiation media results in their maturation into late-stage erythroblasts and reticulocytes.

The invention provides compositions and method for expanding human erythroblasts for an extensive period of time. This is because the invention provides compositions and methods of generating ESREs which are able to undergo extensive self-renewal yet retain the ability to differentiate into RBCs. ESREs of the invention can be used to produce large quantities of mature red blood cells in vitro.

In one embodiment, present invention provides compositions and methods for making and using erythroid cells and enucleated erythroid cells derived from pluripotent stem cells.

The invention therefore also provides cells differentiated with respect to human ESRE, wherein the cells are the progeny of a human ESRE. A "progeny" of an ESRE refers to any and all cells derived from ESRE as a result of clonal proliferation or differentiation. As used herein, a "progenitor cell" is a parent cell committed to give rise to a distinct cell lineage by a series of cell divisions. Specific progenitor cell types may sometimes be identified by markers. A "precursor cell" refers to a cell from which another cell is formed. It encompasses a cell that precedes the existence of a later, more developmentally mature cell. In contrast to the maturation of progenitor cells, which is marked by cell division, the developmental maturation of a precursor cell may include any number of processes or events, including, but not limited to, differential gene expression, or change in size, morphology, or location. As used herein, both progenitor and precursor cells are progeny of and distinct from a pluripotent stem cell. A "developmental intermediate" cell refers to any cell that is either a progenitor or precursor cell that is distinct from the pluripotent stem cells and the ultimately differentiated cell type.

ESRE of the invention include ESRE populations and pluralities of ESRE (and progeny thereof), and cultures of ESRE (cell cultures, and progeny cultures). A population or plurality or culture of ESRE (or progeny thereof) means that there are a collection of such cells. In various embodiments, ESRE population, plurality of ESRE or culture of ESRE (or progeny thereof) include human ESRE that represent at least 25%, 50%, 75%, 90% or more of the total number of cells in the population or plurality or culture.

In a population or plurality of ESRE, or in a culture of ESRE, a majority of cells, but not all cells present may or may not express a particular phenotypic marker indicative of an ESRE. Such cells are typically present in the population, plurality or culture at a smaller percentage of the total number of ESRE present. In various embodiments, an ESRE population, plurality of ESRE or culture of ESRE include cells in which greater than about 20%, 30%, 40%, 50%, 60%, 70%, 80%, 90%-95% or more (e.g., 96%, 97%, 98%, etc.) of the cells express a particular phenotypic marker.

The presence or absence of a given phenotypic marker can be determined using the methods disclosed elsewhere herein. Thus, the presence or absence of a given phenotypic marker can be determined by an antibody that binds to the marker. Accordingly, marker expression can be determined by an antibody that binds to each of the respective markers in order to indicate which or how many ESRE are present in a given population, plurality or culture of ESRE expresses the marker. Additional methods of detecting these and other phenotypic markers are known to one of skill in the art.

In one embodiment, the present invention provides ESRE produced by methods of the invention. In one embodiment, the present invention provides erythroid cells produced by methods of the invention. In one embodiment, the present invention provides RBCs produced by methods of the invention.

ESREs of the invention offer an opportunity to generate RBCs in sufficient quantities to provide a safe and an ample alternative source of cells for transfusion, as well as for treating conditions involving defective RBCs (e.g., hypoxia and sickle cell anemia).

Cell Culture

The present invention arises from the unexpected finding that a human cell population was generated that appear morphologically to represent committed primary erythroblasts, but possess limitless proliferation potential while maintaining the ability to produce enucleated red blood cells (RBCs). Therefore ESREs serves as a viable system for the ex vivo production of blood. In one embodiment, the ESREs exhibit continuous self-renewal for a period of at least 45 days.

The invention also is based on the discovery that human erythroblasts were able to be expanded through a long period of time (e.g., through 45 days of continuous culture) to allow for the massive production of RBCs or reticulocytes from a human embryonic stem cells, human induced-Pluripotent Stem (iPS) cells, and the like. In one embodiment, the invention provides compositions and methods of producing human ESREs whereby the ESREs provide a source of generating a massive amount of RBCs.

Cell cultures of ESRE can take on a variety of formats. For instance, an "adherent culture" refers to a culture in which cells in contact with a suitable growth medium are present, and can be viable or proliferate while adhered to a substrate. Likewise, a "continuous flow culture" refers to the cultivation of cells in a continuous flow of fresh medium to maintain cell viability, e.g. growth.

In one embodiment, the invention includes a culture system comprising at least RBC derived from an ESRE. In various embodiments described elsewhere herein, the invention includes a method of using the ESRE-derived RBC cell culture system of the invention to conduct RBC cell differentiation analyses, to screen for and identify modulators of RBC cell differentiation, and to monitor the effect of modulators of RBC cell differentiation.

The culture system of the invention can include any kind of substrate, surface, scaffold or container known in the art useful for culturing cells. Non-limiting examples of such containers include cell culture plates, dishes and flasks. Other suitable substrates, surfaces and containers are described in Culture of Animal Cells: a manual of basic techniques (3rd edition), 1994, R. I. Freshney (ed.), Wiley-Liss, Inc.; Cells: a laboratory manual (vol. 1), 1998, D. L. Spector, R. D. Goldman, L. A. Leinwand (eds.), Cold Spring Harbor Laboratory Press; Embryonic Stem Cells, 2007, J. R. Masters, B. O. Palsson and J. A. Thomson (eds.), Springer; Stem Cell Culture, 2008, J. P. Mather (ed.) Elsevier; and Animal Cells: culture and media, 1994, D. C. Darling, S. J. Morgan John Wiley and Sons, Ltd. In some embodiments, the culture system comprises a two-dimensional scaffold. In other embodiments, the culture system comprises a three-dimensional scaffold.

Human ESRE and their progeny include individual cells, and populations and pluralities of cells that are isolated or purified. As used herein, the terms "isolated" or "purified" refers to made or altered "by the hand of man" from the natural state (i.e., when it has been removed or separated from one or more components of the original natural in vivo environment.) An isolated composition can but need not be substantially separated from other biological components of the organism in which the composition naturally occurs. An example of an isolated cell would be an ESRE obtained from a subject such as a human. "Isolated" also refers to a composition, for example, an ESRE separated from one or more contaminants (i.e. materials and substances that differ from the cell). A population, plurality or culture of ESRE (or their progeny) is typically substantially free of cells and materials with which it is be associated in nature. The term "purified" refers to a composition free of many, most or all of the materials with which it typically associates with in nature. Thus, an ESRE or its progeny is considered to be substantially purified when separated from other tissue components. Purified therefore does not require absolute purity. Furthermore, a "purified" composition can be combined with one or more other molecules. Thus, the term "purified" does not exclude combinations of compositions. Purified can be at least about 20%, 30%, 40%, 50%, 60% or more by numbers or by mass. Purity can also be about 70% or 80% or more, and can be greater, for example, 90% or more. Purity can be less, for example, in a pharmaceutical carrier the amount of a cells or molecule by weight % can be less than 50% or 60% of the mass by weight, but the relative proportion of the cells or molecule compared to other components with which it is normally associated with in nature will be greater. Purity of a population or composition of cells can be assessed by appropriate methods that would be known to the skilled artisan.

ESRE of the invention and their progeny can be sterile, and maintained in a sterile environment. Such ESRE, pluralities, populations, and cultures thereof can also be included in a medium, such as a liquid medium suitable for administration to a subject (e.g., a mammal such as a human).

Methods for producing ESREs and their differentiated progeny are provided herein. In one embodiment, a method includes obtaining a tissue or blood sample, cloning one or more cells from the sample, selecting one or more cells based upon morphology or growth rate or phenotypic marker expression profile, thereby isolating an ESRE.

Methods for producing ESRE populations and pluralities of ESREs are also provided. In such methods, expanding ESREs for a desired number of cell divisions (doublings) thereby produces increased numbers or a population or plurality of ESRE. Relative proportions or amounts of ESRE within cell cultures include 20%, 30%, 40%, 50%, 60%, 70%, 80%, 90% or more ESRE in a population or plurality of cells.

Methods for producing a differentiated progeny cell of an ESRE (e.g., a progenitor cell, a precursor cell, a developmental intermediate, a differentiated cell, RBCs) from ESRE are also provided.

In various embodiments, the method of making a RBC derived from an ESRE comprises a multi-step method of: 1) generating ESREs from a stem cell; and 2) differentiating the ESREs into RBCs. In one embodiment, the invention includes a RBC cell derived from an ESRE. In one embodiment, the invention includes a method of making a RBC cell derived from an ESRE. In one embodiment, the ESREs can be expanded through at least 30 days of continuous culture. In one embodiment, the ESREs can be expanded through at least 35 days of continuous culture. In one embodiment, the ESREs can be expanded through at least 40 days of continuous culture. In one embodiment, the ESREs can be expanded through at least 45 days of continuous culture. In one embodiment, the ESREs can be expanded through at least 50 days of continuous culture. In one embodiment, the ESREs can be expanded through at least 55 days of continuous culture. In one embodiment, the ESREs can be expanded through at least 60 days of continuous culture. In one embodiment, the ESREs can be expanded through at least 65 days of continuous culture. In one embodiment, the ESREs can be expanded through at least 70 days of continuous culture. In one embodiment, the ESREs can be expanded through at least 75 days of continuous culture. In one embodiment, the ESREs can be expanded through at least 80 days of continuous culture. In one embodiment, the ESREs can be expanded through at least 85 days of continuous culture. In one embodiment, the ESREs can be expanded through at least 90 days of continuous culture. In one embodiment, the ESREs can be expanded through at least 95 days of continuous culture. In one embodiment, the ESREs can be expanded through at least 100 days of continuous culture.

In various embodiments, the method of making a RBC derived from an ESRE comprises a multi-step method of: 1) generating ESREs from a stem cell; 2) differentiating ESREs into RBCs. In one embodiment, the invention includes a RBC cell derived from a stem cell. In one embodiment, the invention includes a method of making a RBC cell derived from a stem cell. In one embodiment, the RBCs are generated from a stem cell according to the present invention in about at least 30 days, 35 days, 40 days, 45 days, 50 days, 55 days, 60 days, 65 days, 70 days, 75 days, 80 days, 85 days, 90 days, 95 days, or 100 days.

The quality of the RBCs derived from ESRE may be detected morphologically, as well as expression of cell differentiation-related markers. The ability of the RBCs derived from ESRE to function in vivo may be studied using animal models or in clinical trials.

In various embodiments, storing, stored, preserving and preserved stem cells and conditioned medium include freezing (frozen) or storing (stored) ESRE and conditioned medium, such as, for example, individual ESRE or their progeny, a population or plurality of ESRE or their progeny, a culture of ESRE or their progeny, co-cultures and mixed populations of ESRE or their progeny and other cell types and conditioned medium. ESRE, their progeny, and their conditioned medium can be preserved or frozen, for example, under a cryogenic condition, such as at −20° C. or less, e.g., −70° C. Preservation or storage under such conditions can include a membrane or cellular protectant, such as dimethylsulfoxide (DMSO).

ESRE, a population or plurality or culture of ESRE, progeny of ESRE (e.g., any clonal progeny or any or all various developmental, maturation and differentiation stages) and conditioned medium of ESRE cells can be used for various applications, can be used in accordance with the methods of the invention including treatment and therapeutic methods. The invention therefore provides in vivo and ex vivo treatment and therapeutic methods that employ ESRE, populations and pluralities and cultures of ESRE, progeny of ESRE and conditioned medium of ESRE.

ESRE, a population or plurality or culture of ESRE, progeny of ESRE (e.g., any clonal progeny or any or all various developmental, maturation and differentiation stages) and conditioned medium of ESRE cells can be administered to a subject, or used to implant or transplant as a cell-based or medium based therapy to provide a benefit to a subject.

Therapy

The invention contemplates use of the cells of the invention in both in vitro and in vivo settings. Thus, the invention provides for use of the cells of the invention for research purposes and for therapeutic or medical/veterinary purposes. In research settings, an enormous number of practical applications exist for the technology. One example of such applications is use of the cells of the invention to massively produce RBCs. Massive production of RBCs is beneficial for at least clinical transfusions.

In one embodiment, the RBCs generated from the compositions and methods of the invention have characteristics of adult and functional native RBCs. In some instances, the RBCs generated from the compositions and methods of the invention have all the characteristics of adult and functional native RBCs.

In one embodiment, the present invention thus provides an in vitro method for producing enucleated erythrocytes (including reticulocytes and mature red blood cells).

The method of the invention allows for the massive production of a homogenous population of enucleated erythrocytes. The potential cell yields are compatible with the clinical requirements for transfusion. In some instances, the levels of expanding cells and generating RBCs can be from $10^7$- to $10^{60}$-fold. Apart from the interest for transfusion in terms of supply and infectious safety, the invention makes it possible to easily produce several units derived from one donor and/or autologous transfusion patient.

The invention is also advantageous with regard to transfusion efficacy. It allows the infusion of a cell population homogeneous in age with a life span close to 120 days, whereas the mean half-life of the RBCs obtained from a donor is 28 days due to the simultaneous presence of cells of variable age. This would reduce the number of transfusions that are needed.

In some embodiments, the ESRE or their progeny can be autologous with respect to the subject; that is, the ESRE used in the method (or to produce the conditioned medium) were obtained or derived from a cell from the subject that is treated according to the method. In other embodiments, the ESRE, the progeny of ESRE or conditioned medium of ESRE or their progeny can be allogeneic with respect to the subject; that is, the ESRE used in the method (or to produce the conditioned medium) were obtained or derived from a cell from a subject that is different from the subject that is treated according to the method.

The methods of the invention also include administering ESRE, progeny of ESRE, or conditioned medium of ESRE prior to, concurrently with, or following administration of additional pharmaceutical agents or biologics. Pharmaceutical agents or biologics may activate or stimulate ESRE or their progeny. Non-limiting examples of such agents include, for example: EPO, SCF, and IGF1.

Genetic Modification

The cells of the invention whether genetically modified or not, can be used to treat a disease or disorder of the blood such as a hemostatic disorder. In one embodiment, the cells of the invention can be used to treat an acute bleeding episode in a subject with a hemostatic disorder.

In the context of gene therapy, the cells of the invention can be treated with a gene of interest prior to delivery of the cells into the recipient. In some cases, such cell-based gene delivery can present significant advantages of other means of gene delivery to the subject, such as administration of a recombinant protein or a form of gene therapy to the subject. Delivery of a therapeutic gene that has been pre-inserted into cells avoids the problems associated with penetration of gene therapy vectors into target cells of the subject.

Accordingly, the invention provides the use of genetically modified cells that have been cultured according to the methods of the invention. Genetic modification may, for instance, result in the expression of exogenous genes ("transgenes") or in a change of expression of an endogenous gene. Such genetic modification may have therapeutic benefit. Alternatively, the genetic modification may provide a means to track or identify the cells so-modified, for instance, after implantation of a composition of the invention into an individual. Tracking a cell may include tracking migration, assimilation and survival of a transplanted genetically-modified cell. Genetic modification may also include at least a second gene. A second gene may encode, for instance, a selectable antibiotic-resistance gene or another selectable marker.

Proteins useful for tracking a cell include, but are not limited to, green fluorescent protein (GFP), any of the other fluorescent proteins (e.g., enhanced green, cyan, yellow, blue and red fluorescent proteins; Clontech, Palo Alto, Calif.), or other tag proteins (e.g., LacZ, FLAG-tag, Myc, $His_6$, and the like).

When the purpose of genetic modification of the cell is for the production of a biologically active substance, the substance will generally be one that is useful for the treatment of a given disorder. For example, it may be desired to genetically modify cells so that they secrete a certain factor product associated with blood or bone.

The cells of the present invention can be genetically modified by having exogenous genetic material introduced into the cells, to produce a molecule such as a clotting factor. In addition, by having the cells genetically modified to produce such a molecule, the cell can provide an additional therapeutic effect to the mammal when transplanted into a mammal in need thereof. For example, the genetically modified cell can secrete a molecule that is beneficial to cells neighboring the transplant site in the mammal.

The cells of the invention may be genetically modified using any method known to the skilled artisan. See, for instance, Sambrook et al. (2001, Molecular Cloning: A Laboratory Manual, Cold Spring Harbor Laboratory Press, Cold Spring Harbor, N.Y.), and in Ausubel et al., Eds, (1997, Current Protocols in Molecular Biology, John Wiley & Sons, New York, N.Y.). For example, a cell may be exposed to an expression vector comprising a nucleic acid including a transgene, such that the nucleic acid is introduced into the cell under conditions appropriate for the transgene to be expressed within the cell. The transgene generally is an expression cassette, including a polynucleotide operably linked to a suitable promoter. The polynucleotide can encode a protein, or it can encode biologically active RNA (e.g., antisense RNA or a ribozyme).

Within the expression cassette, the coding polynucleotide is operably linked to a suitable promoter. Examples of suitable promoters include prokaryotic promoters and viral promoters (e.g., retroviral ITRs, LTRs, immediate early viral promoters (IEp), such as herpesvirus IEp (e.g., ICP4-IEp and ICPO-IEEp), cytomegalovirus (CMV) IEp, and other viral promoters, such as Rous Sarcoma Virus (RSV) promoters, and Murine Leukemia Virus (MLV) promoters). Other suitable promoters are eukaryotic promoters, such as enhancers (e.g., the rabbit .beta.-globin regulatory elements), constitutively active promoters (e.g., the .beta.-actin promoter, etc.), signal specific promoters (e.g., inducible promoters such as a promoter responsive to RU486, etc.), and tissue-specific promoters. It is well within the skill of the art to select a promoter suitable for driving gene expression in a predefined cellular context. The expression cassette can include more than one coding polynucleotide, and it can include other elements (e.g., polyadenylation sequences, sequences encoding a membrane-insertion signal or a secretion leader, ribosome entry sequences, transcriptional regulatory elements (e.g., enhancers, silencers, etc.), and the like), as desired.

The expression cassette containing the transgene should be incorporated into a genetic vector suitable for delivering the transgene to the cells. Depending on the desired end application, any such vector can be so employed to genetically modify the cells (e.g., plasmids, naked DNA, viruses such as adenovirus, adeno-associated virus, herpesviruses, lentiviruses, papillomaviruses, retroviruses, etc.). Any method of constructing the desired expression cassette within such vectors can be employed, many of which are well known in the art (e.g., direct cloning, homologous recombination, etc.). The choice of vector will largely determine the method used to introduce the vector into the cells (e.g., by protoplast fusion, calcium-phosphate precipitation, gene gun, electroporation, DEAE dextran or lipid carrier mediated transfection, infection with viral vectors, etc.), which are generally known in the art.

Examples of techniques sufficient to direct persons of skill through in vitro amplification methods, including the polymerase chain reaction (PCR), the ligase chain reaction (LCR), and other DNA or RNA polymerase-mediated techniques are found in Sambrook et al., MOLECULAR CLONING: A LABORATORY MANUAL, volumes 1-3 ($3^{rd}$ed., Cold Spring Harbor Press, NY 2001).

Once the nucleic acid for a protein is cloned, a skilled artisan may express the recombinant gene(s) in a variety of ways. It is expected that those of skill in the art are knowledgeable in the numerous expression systems available for expressing the desired transgene.

In one embodiment, the desired transgene is a clotting factor. The clotting factor can include any molecule that has clotting activity or activates a molecule with clotting activity. The clotting factor can be comprised of a polypeptide, a small organic molecule, or a small inorganic molecule. The clotting factor can be a mutated clotting factor or an analog of a clotting factor so long as it maintains at least some clotting activity. The clotting factor can be, as an example, but not as a limitation factor VII, including B domain deleted factor VIII, factor IX (U.S. Pat. No. 4,994,371), factor XI, factor XII, fibrinogen, prothrombin, factor V, factor VII, factor X, or factor XIII. In one embodiment, the clotting factor is factor VII or factor VIIa. In another embodiment, the clotting factor is a mutated factor VII or VIIa (see, e.g., Persson, et al. 2001, Proc. Natl. Acad. Sci. USA 98:13583). The clotting factor can be a factor that participates in the extrinsic pathway. The clotting factor can be a factor that participates in the intrinsic pathway. Alternatively, the clotting factor can be a factor that participates in both the extrinsic and intrinsic pathway.

The clotting factor can be a human clotting factor or a non-human clotting factor, e.g., derived from a non-human primate, a pig, or any mammal. The clotting factor can be chimeric clotting factor, e.g., the clotting factor can comprise a portion of a human clotting factor and a portion of a porcine, or any non-human clotting factor or a portion of a first non-human clotting factor and a portion of a second non-human clotting factor.

Therapy

The cells of the invention, whether genetically modified or not, can be used to treat any hemostatic disorder. In one embodiment, the hemostatic disorders that may be treated by administering cells of the invention include, but are not limited to, hemophilia A, hemophilia B, von Willebrand's disease, factor XI deficiency (PTA deficiency), factor XII deficiency, as well as deficiencies or structural abnormalities in fibrinogen, prothrombin, factor V, factor VII, factor X, or factor XIII.

The cells of the invention can be used to prophylactically treat a subject with a hemostatic disorder. The cells of the invention can be used to treat an acute bleeding episode in a subject with a hemostatic disorder.

In one embodiment, the hemostatic disorder is the result of a deficiency in a clotting factor, e.g., factor IX, factor VII, factor VII. In another embodiment, the hemostatic disorder can be the result of a defective clotting factor, e.g., von Willebrand's factor.

In another embodiment, the hemostatic disorder can be an acquired disorder. The acquired disorder can result from an underlying secondary disease or condition. The unrelated condition can be, as an example, but not as a limitation, cancer, an auto-immune disease, or pregnancy. The acquired disorder can result from old age or from medication to treat an underlying secondary disorder (e.g. cancer chemotherapy).

In another embodiment, the invention relates to a method of treating a subject with a hemostatic disorder comprising administering a therapeutically effective amount of a cell of the invention genetically modified to express at least one clotting factor in combination with a second factor wherein the second factor can be at least one other clotting factor or-agent that promotes hemostasis. In one embodiment, the second factor or agent that promotes hemostasis can be any therapeutic with demonstrated clotting activity. As an example, but not as a limitation, the clotting factor or hemostatic agent can include factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include anti-fibrinolytic drugs, e.g., epsilon-aminocaproic acid, tranexamic acid.

In Vitro Screening Methods

According to the present invention, the cells of the invention are engineered to comprise a recombinant promoter (e.g., globin gene promoter) comprising a detectable reporter operably linked to a gene promoter. Candidate agents are added to in vitro cell cultures of host cells and the activity of the reporter gene is measured. Various in vitro systems can be used to analyze the effects of a new compound on reporter gene expression under control of the desired promoter.

Reporter genes for use in the invention encode detectable proteins, include, but are by no means limited to, chloramphenicol transferase (CAT), beta-galactosidase (beta-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

The host cell screening system of the invention permits two kinds of assays: direct activation assays (agonist screen) and inhibition assays (antagonist screen). An agonist screen involves detecting changes in the level of expression of the reporter gene by the host cell contacted with a test compound; generally, reporter gene expression decreases. If the reporter gene is expressed, the test compound has not affected the promoter; if the reporter gene expression decreases, the test compound is a candidate for developing a suppressive drug against the promoter.

Agents according to the invention may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277; 5,679,582; and 6,020,141). Such high-throughput screening methods are particularly preferred. Alternatively, simple reporter-gene based cell assays such as the one described here are also highly desirable. The use of high-throughput screening assays to test for agents is greatly facilitated by the availability of large amounts of purified polypeptides, as provided by the invention.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Extensively Self-Renewing Erythroblasts (ESREs)

The results presented herein show the development and characterization of extensively self-renewing erythroblasts (ESREs). The results demonstrate that ESREs are cells that represent primary erythroblasts, but possess apparently limitless proliferation potential while maintaining the ability to produce enucleated red blood cells (RBCs). Therefore ESREs offer the promise of serving as the foundation of a viable system for the ex vivo production of blood.

Experiments were designed to (1) allowing the production of human RBCs; (2) demonstrate that the currently prohibitive costs of large-scale culture, involving highly expensive growth factors and reagents, can be reduced to a more practical level; and (3) demonstrate that ESREs can be used as an ex vivo model for erythropoiesis with practical benefits in drug screening and bioengineering.

Definitive, Steady-State Erythropoiesis

Humans synthesize more than 2 million RBCs every second to maintain a steady-state red cell mass of ~$2.5 \times 10^{13}$ RBCs. As summarized in FIG. 1A, these massive numbers of RBCs are derived from a small number of hematopoietic stem cells (HSCs) that differentiate into lineage-restricted progenitors that are capable of forming colonies of erythroid cells in semisolid media. Immature erythroid progenitors (BFU-E) differentiate into late-stage erythroid progenitors (CFU-E) that mature into morphologically recognizable erythroid precursors. These proerythroblasts in turn physically interact with macrophage cells in the bone marrow and undergo 3-4 maturational cell divisions, during which they accumulate hemoglobin, decrease in size, and condense their nuclei (Bessis et al., 1978, Blood Cells 4:155-174). CFU-E and immature erythroid precursors are exquisitely dependent on the cytokine erythropoietin (EPO) for their survival (Koury and Bondurant, 1990, Science 248:378-381). The most mature erythroid precursors, termed orthochromatic erythroblasts, undergo nuclear extrusion to form young RBCs (reticulocytes). Reticulocytes lose all cellular organelles, remodel their cytoskeleton to take on a biconcave shape, and enter the bloodstream to circulate as mature RBCs for 120 days.

Erythroblast Self-Renewal

Erythroid "progenitors" can be induced to undergo relatively limited ($10^5$- to $10^6$-fold) amplification in vitro when cultured with EPO, SCF and dexamethasone (von Lindern et al., 1999, Blood 94:550-559; FIG. 1B, upper section). Signaling pathways initiated by EPO receptor (EPOR) and SCF receptor (ckit) synergize to enhance erythroid precursor survival and proliferation, while glucocorticoids inhibit erythroid differentiation (Panzenbock et al., 1998, Blood 92:3658-3668; von Lindern et al., 1999, Blood 94:550-559). These cultured bone marrow derived erythroid "progenitors" retain the ability to differentiate into enucleated erythrocytes when cultured in the presence of EPO alone, indicating that SCF and dexamethasone stimulate erythroblast self-renewal.

Figure 2:
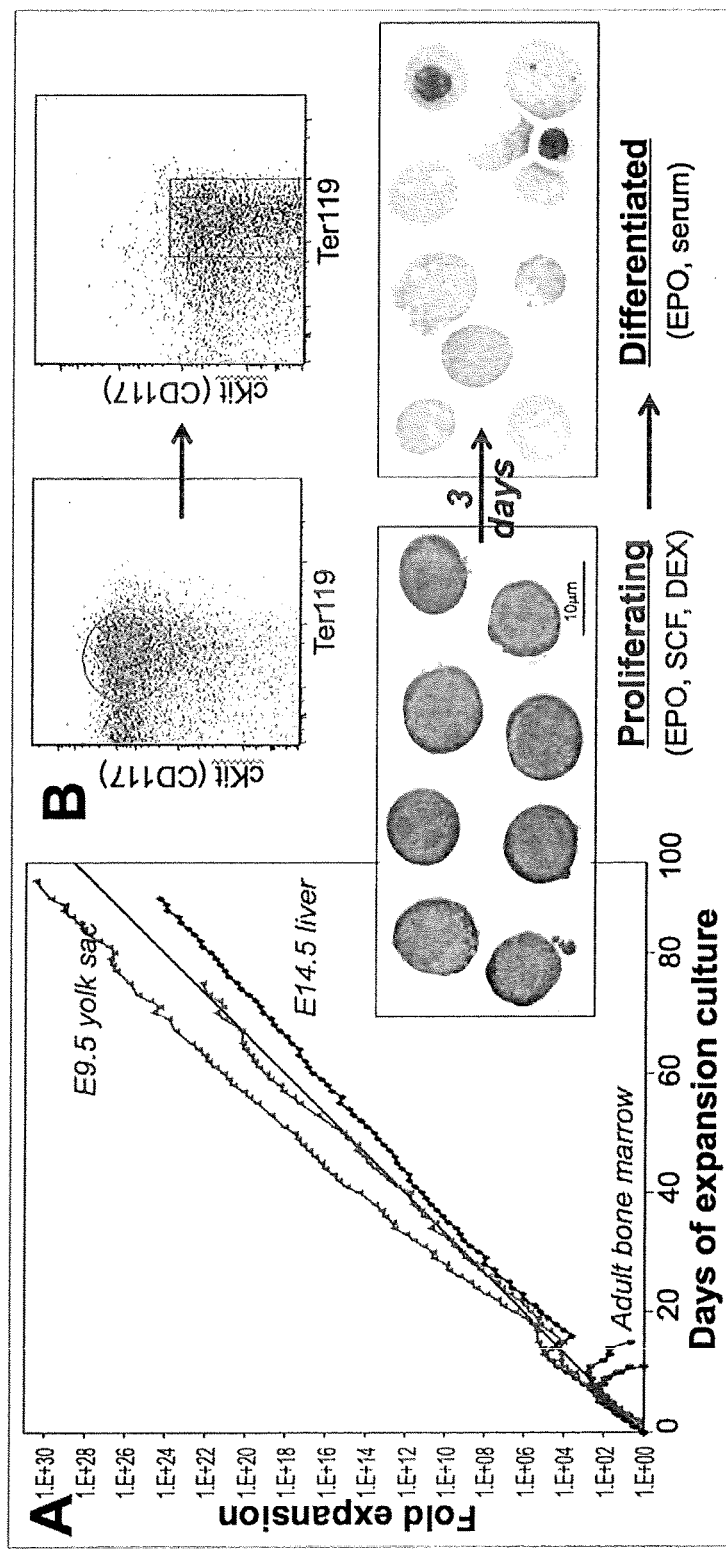
FIG. 2, comprising

It has been discovered that erythroid cells derived from the murine yolk sac and early fetal liver are capable not only of restricted, but also of extensive ($10^7$- to $10^{60}$-fold) ex vivo proliferation when cultured in EPO, SCF, and dexamethasone (England et al., 2011, Blood 117:2708-2717; FIG. 1B, lower section; FIG. 2A). Furthermore, this proliferative capacity is far greater than previously found in cultures derived from late fetal liver- or postnatal bone marrow. These cells maintain a proerythroblast cell morphology throughout their ex vivo culture (FIG. 2B), and they express high amounts of ckit (CD117) with low levels of the ter119 (a marker of late erythroid maturation) on their cell surface (FIG. 2B). CFSE-labeling studies indicate that the vast majority of the erythroblasts in culture divide daily (England et al., 2011, Blood 117:2708-2717). Despite prolonged culture with daily cell divisions extending for many months, these immature erythroblasts remain dependent on EPO, SCF, and dexamethasone and preserve their potential to mature into enucleated RBCs (8-16 RBCs per progenitor cell) when transferred into media lacking dexamethasone (FIG. 2B). Erythroid maturation is associated with loss of ckit and upregulation of ter119 cell surface expression (FIG. 2B). Taken together, these findings indicate that these proliferating erythroid cells 1) are undergoing symmetrical self-renewal cell divisions, 2) are at the proerythroblast stage of maturation, only 3-4 cell divisions upstream of a RBC, and 3) can mature into reticulocytes in vitro. These cells are termed "extensively self-renewing erythroblasts" (ESREs). Regardless of their embryonic origins, ESRE-derived reticulocytes express adult-type ($\alpha$, $\beta 1$, and $\beta 2$) globins, similar to definitive RBCs produced in the marrow.

Development of the Hematopoietic System

In the adult, all blood cells originate from HSCs that first emerge as cell clusters from "hemogenic" endothelium in several vascular beds beginning at E10.5 and 5 weeks of gestation in the mouse and human embryo, respectively (Muller et al., 1994, Immunity 1:291-301; Ivanovs et al., 2011, J Exp Med 208, 2417-2427). HSC subsequently seed the fetal liver and perinatal marrow to sustain life-long hematopoiesis.

Pre-HSC Hematopoiesis

Two transient waves of hematopoietic progenitors arising in the yolk sac of the mouse embryo prior to HSC have been identified (Palis et al., 1999, Development 126:5073-5084). The first wave consists of primitive erythroid progenitors that generate the first large, nucleated primitive RBCs in the mouse. The second wave consists of definitive erythroid progenitors (BFU-E), accompanied by multiple myeloid progenitors (Palis et al., 1999, Development 126:5073-5084; Palis et al., 2001, Proc Natl Acad Sci USA 98:4528-4533). Transient primitive and definitive waves of erythropoiesis have also been identified in human and zebrafish embryos (Migliaccio et al., 1986, J Clin Invest 78:51-60; Bertrand et al., 2007, Development 134:4147-4156), indicating the evolutionary conservation of pre-HSC hematopoiesis. Similar findings in mouse ES cells (Keller et al., 1993, Mol Cell Biol 13:473-486) and in human ES cells (see FIG. 3), led to the hypothesize that differentiating ES cells recapitulate pre-HSC embryonic hematopoiesis. The studies in the mouse embryo and mouse ES cells indicate that ESREs are generated from the definitive erythroid lineage and not from the primitive erythroid lineage, which lacks GR expression and is incapable of in vitro self-renewal (England et al., 2011, Blood 117:2708-2717). Thus, ESREs can be derived exclusively from a narrow window of erythroid development, corresponding to a transient wave of definitive erythropoiesis that originates in the embryonic yolk sac and then migrates to the early fetal liver.

Murine ESRE can Generate a Wave of Mature RBCs in Vivo

Figure 3:
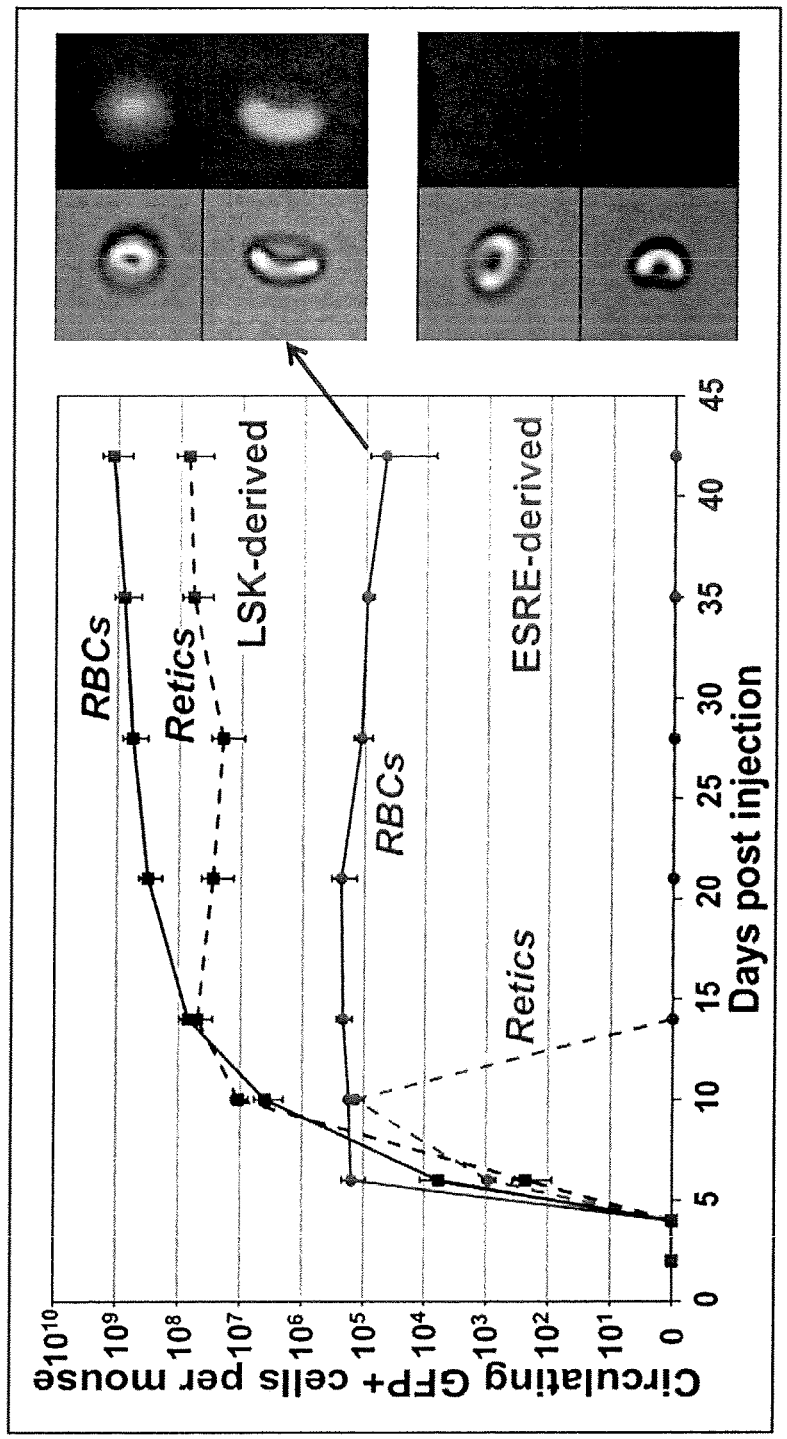
FIG. 3 is an image showing circulation of reticulocytes and mature RBCs in NSG mice injected IV with immature hematopoietic marrow progenitors from mouse bone marrow (LSK) or with ESRE derived from UBC-GFP mice. Upon differentiation in vivo, ESRE give rise to a transient wave of GFP+ RBCs, similar in size and morphology to wild-type RBCs (right panels).

To test the capacity of ESRE to differentiate in vivo, ESRE cultures were generated from UBC-GFP mice. Control LSK cells, sorted from the marrow of UBC-GFP mice, were injected IV into other recipient NSG mice and gave rise, beginning at day 5, to persistent reticulocytes and mature RBCs, consistent with their engraftmant (FIG. 3, black lines). Importantly, UBC-GFP-derived ESRE, grown in self-renewing cultures for 77 days, were injected IV into recipient NSG mice. These GFP+ ESRE gave rise beginning at day 5 to a transient wave of reticulocytes and mature RBCs (FIG. 3, red lines). Analysis of these ESRE-derived RBCs by imaging flow cytometry indicates that they have normal size and shape when compared to wild-type (non-GFP) RBCs (FIG. 3, right panels). Taken together, these data provide evidence that ESRE, despite prolonged culture, are not transformed and can differentiate in vivo to into fully mature RBCs.

Primitive and Definitive/EMP Emergence in Differentiating Human ES/EBs.

Figures 4A, 4B, 4C, 4D:
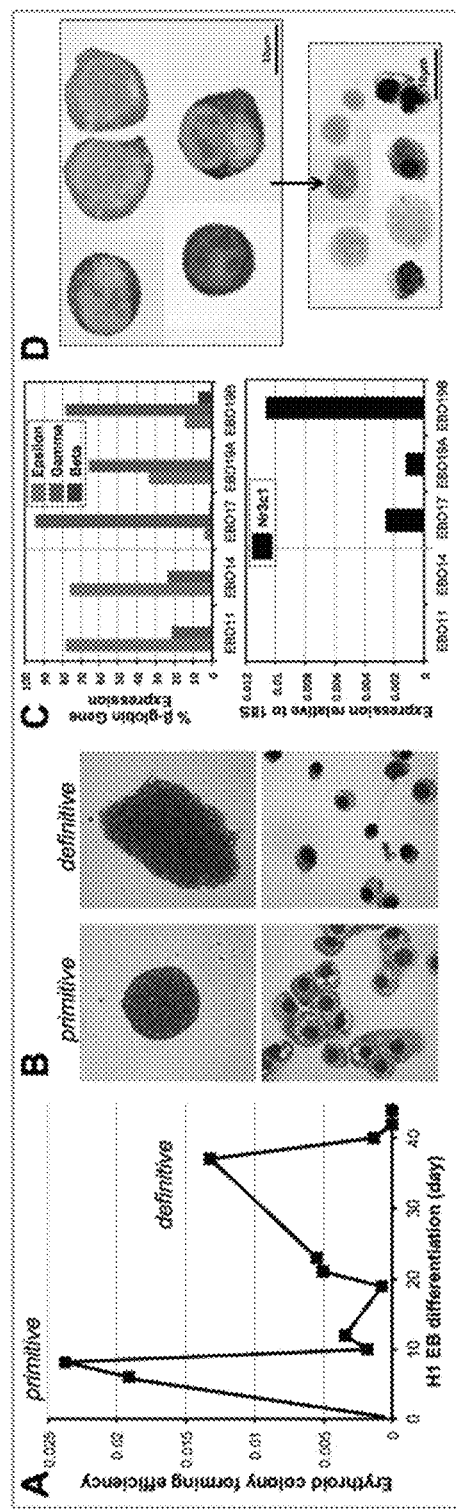
FIGS. 4A through 4I, is a series of images showing emergence of erythroid potential in human H1 ES/EBs.

Undifferentiated H1 (WA01, WiCell Research Institute) human ES cells were cultured feeder-free with mTeSR1 media (Stem Cell Technologies) on matrigel-coated plates with daily media changes. Cells were enzymatically harvested with Collagenase IV, passaged weekly, and differentiated to blood cell fates in serum-free conditions as outlined in Table 1. The results indicated that this human ES cell differentiation protocol led to the emergence of 2 waves of erythroid progenitors (FIG. 4A), which contained colonies having the morphology and cellular content typically associated with primitive and definitive erythroid lineages, respectively (FIG. 4B). Gene expression of 5 isolated colonies from day 11-19 EBs were analyzed. As shown in FIG. 4C, the colonies from day 11 and day 14 EBs expressed predominantly $\epsilon$-globin but do not express Nr3c1, the gene encoding glucocorticoid receptor (GR). These data are consistent with the findings in the mouse, where primitive erythroblasts express predominantly embryonic globins, but not GR (England et al., 2011, Blood 117:2708-2717). The colonies from day 17 and day 19 EBs expressed predominantly $\gamma$-globin, as well as GR, consistent with a definitive erythroid identity (FIG. 4B). These data are consistent with the sequential waves of primitive and definitive erythropoiesis seen in mouse yolk sacs (Palis et al., 1999, Development 126:5073-5084) and murine ES cell differentiations (Keller et al., 1993, Mol Cell Biol 13:473-486). Experiments were designed to further characterize the kinetics of hematopoiesis in differentiating human ES cells through the prism of normal embryonic hematopoiesis. Without wishing to be bound by any particular theory, it is believed that the emergence of hematopoietic potential in human ES cells is characterized by overlapping waves of primitive and EMP/definitive (pre-HSC) hematopoiesis.

Erythroid lineage-specific markers are used to further distinguish primitive and definitive erythroid cells. Experiments can be designed to test for genes that are differentially expressed in the colonies derived from the first and second waves of erythroid progenitors emerging from differentiating human ES cells. It is desirable to identify 2-4 erythroid lineage-specific markers to unequivocally differentiate primitive and definitive erythroid potential emerging differentiating human ES cells.

Without wishing to be bound by any particular theory, it is believed that differentiating human ES cells will recapitulate early embryonic events and lead to the generation both of primitive and of EMP/definitive hematopoietic progenitor cell populations. In addition, it is expected a set of erythroid lineage-specific markers can facilitate the categorical identification of primitive and definitive erythroid cells.

Self-Renewing Definitive Erythroblasts can be Derived from H1 Human ES Cells.

Having defined the emergence of definitive erythropoiesis in H1 human ES/EBs, erythroblast self-renewing cultures were initiated (EPO, SCF, dexamethasone) using day 16-19 EB cells. The initial cultures have given rise to a uniform population of immature erythroblasts (FIG. 4D, upper panel) that continued to proliferate for 20-30 days. These erythroblasts differentiated into orthochromatic erythroblasts and reticulocytes when placed in maturation media containing EPO and insulin (FIG. 4D, lower panel). Self-renewing human erythroblasts expressed predominantly γ-globin along with lower levels of ε-globin, and upregulated the adult β-globin gene upon maturation. These data provide important evidence that definitive self-renewing erythroblasts can be generated from human ES/EBs Generate Human ESREs and Optimize their Proliferation and Maturation Deriving erythroblasts with extensive self-renewal capacity from human ES cells avoids the practical and ethical concerns of using human embryos. The results indicate that the current human ES differentiation protocol (Table 1) facilitates the subsequent generation of human self-renewing erythroblasts (FIG. 4D). It is important to show that these erythroblasts can self-renew for extensive periods of time. Cultures of erythroblasts from human cord blood can be maintained for 10-15 days before all the erythroblasts spontaneously differentiate, consistent with their restricted self-renewal capacity, as previously defined by others (von Lindern et al., 1999, Blood 94:550-559). Without wishing to be bound by any particular theory, it is desirable that the ESRE cultures continue to expand robustly for at least 3 times longer as evidence of extensive self-renewal. In some instances, it is desirable to generate erythroblast cultures from human ES cells that self-renew for more than 45 days.

ESRE cultures are initiated using differentiated human ES cells from specific days of EB differentiation as discussed elsewhere herein. An exemplary current serum-free human ESRE culture condition includes StemSpan (Stem Cell Technologies), EPO (2 U/ml), SCF (100 ng/ml), dexamethasone ($10^{-6}$M), IGF1 (40 ng/ml) and ExCyte (0.4%; Millipore). Cultures are monitored daily with cell counts, viability measurements, and partial volume changes with fresh media. Cultures of erythroblasts from human cord blood can be maintained for 10-15 days before all the erythroblasts spontaneously differentiate, consistent with their restricted self-renewal capacity, as previously defined by others (von Lindern, 1999). The erythroblast cultures derived from human ES cells are monitored on a daily basis and tested for their capacity to generate erythroblasts with not only restricted, but also extensive, self-renewal capabilities. Embryonic, fetal and adult globin gene expression is characterized by qPCR to verify the "definitive" erythroid (predominantly γ- and β-globin expression) nature of the self-renewing cells. More clear-cut markers of primitive versus definitive erythroid cells can facilitate the identification of definitive erythroblasts.

An important goal is to optimize human erythroblast culture conditions to maximize the potential of embryonic erythroblasts to undergo extensive self-renewal. The current protocol relies on StemSpan SFEM as a basal medium. The results presented herein demonstrate that an expansion media, specifically containing StemSpan™-ACF (Stem Cell Technologies), supports the extensive in vitro self-renewal of human erythroblasts derived from human ES cells. The basal media that supports mouse ESRE proliferation (StemSpan™-SFEM) does not support the extensive proliferative self-renewal of human erythroblasts. Unlike StemSpan™-ACF, initial studies of other basal media, including StemSpan SFEM II and QBSF60 (Quality Biological) did not result in extensive human erythroblast self-renewal. Therefore protocols for culturing mouse cells cannot be applied to culturing human cells.

Other reagents necessary for improving the efficiency with which self-renewing cultures can be derived from human ESCs can be tested. This includes alternate steroids, such as fluticasone proprionate, an extremely potent glucocorticoid agent; our preliminary studies of murine ESREs indicate that doses of fluticasone as low as $10^{-9}$M support erythroblast self-renewal as effectively as $10^{-6}$M dexamethasone. Various lipid additives, including Excyte (Millipore) and Human LDL (Stem Cell Technology) can also be test for to optimizing support human erythroblast self-renewal.

Human erythroblast culture conditions are optimized to maximize the potential of embryonic erythroblasts to undergo extensive self-renewal. The culture conditions are compared to culture conditions derived by others of adult-derived human erythroblasts, such as the HEMA$^{def}$ and the HEMA$^{ser}$ culture conditions (Migliaccio, 2010). A dose-response to different steroids, including fluticasone proprionate, an extremely potent glucocorticoid agent, can be tested to support erythroblast self-renewal. Various lipid additives, including Excyte (Millipore) and Human LDL (Stem Cell Technology) can be tested to optimally support human erythroblast self-renewal.

It is believed that ESREs serve as a renewable source of erythroblasts from which to generate cultured RBCs. By identifying definitive erythroid progenitors in cultures of differentiating/ed human ES cells, cultures of self-renewing human erythroblasts and ultimately human ESREs can be generated. The studies indicate that self-renewing erythroblasts can be generated from human ES cells. It is expected that optimization of human erythroblast self-renewal cultures derived from human ES/iPS cells, as discussed elsewhere herein facilitates the generation of human ESREs. Since ESREs have been generated from fetal and adult mice lacking p53 (von Lindern, 2001; Schmidt, 2005), an alternative approach to the generation of ESREs from human ES cells is knock-down of p53. ESRE from human neonatal and adult sources can be used, if needed, in differentiating human ES cells or the self-renewing erythroblasts derived from human ES cells.

Characterize the Differentiation of Self-Renewing Human Embryonic Erythroblasts into Reticulocytes Mouse self-renewing embryonic erythroblasts can be differentiated into RBCs in vitro using serum-free media containing EPO and insulin (England et al., 2011, Blood 117:2708-2717). Multiple protocols are available to differentiate human immature erythroblasts into reticulocytes (Giarratana 2011). These protocols involve 2, 3 or 4 sequential phases. Imaging flow cytometry is used to quantitate parameters of RBC maturation, including cell size, nuclear condensation, cell shape changes associated with reticulocyte maturation, progressive loss of RNA and mitochondrial content, and enucleation rates. Embryonic, fetal and adult hemoglobins can be quantitated by cellulose acetate electrophoresis. Benzidine positivity, hemoglobin content by spectrophometry, and globin gene expression by qPCR can also be determined on the in vitro differentiated human RBCs.

The ability of self-renewing erythroblasts to differentiate in vivo also can be analyzed using an immunodeficient (NSG) mouse model. 100 million self-renewing erythroblasts derived from human ES cells are injected IV into adult NSG mice and the peripheral blood sampled every 2 days to determine the number of human (glycophorin A+) versus mouse (ter119+) RBCs by FACS. The analysis continues until human RBCs can no longer be detected. To test the ability of in vitro differentiated ESREs to function as a transfusion product, ESRE-derived reticulocytes are injected into adult NSG mice and their numbers are followed over time. The validity of this in vivo experimental model for the study of human RBC function has recently been published (Kobari, 2012). Imaging flow cytometry is used to analyze the size and morphology of circulating human RBCs.

The in vitro differentiation studies can be performed using the human self-renewing erythroblasts currently being derived from human ES cells. Human extensively self-renewing erythroblasts can also be tested for their potential to differentiate into reticulocytes. Mouse erythroblasts undergoing either restricted and extensive self-renewal can differentiate in vitro with high enucleation rates, typically 90-95% (England et al., 2011, Blood 117:2708-2717). Preliminary results suggest that human erythroblasts recapitulate the high enucleation rates. Molecules antagonistic to the action of glucocorticoids can be used to overcome any inherent residual block of erythroid precursor differentiation (Lieberbauer, 2005; Miharada, 2006). Alternative approaches to the differentiation of erythroblasts in vitro include coculture with stromal cells, particularly MS5 cells (Giarratana, 2005). However, these alternative approaches would be used if enucleation rates are consistently <50-60% or the parameters of maturing RBCs, e.g., hemoglobin content, are not close to those of normal RBCs.

Optimize the in Vitro Differentiation of Embryonic Human Erythroblasts Using EPO and Insulin Imaging flow cytometry can be used to quantitate parameters of RBC maturation, including cell size, nuclear condensation, cell shape changes associated with reticulocyte maturation, progressive loss of RNA and mitochondrial content, and enucleation rates. Embryonic, fetal and adult hemoglobins can be quantitated by cellulose acetate electrophoresis. Benzidine positivity, hemoglobin content by spectrophometry, and globin gene expression by qPCR can also be determined on the in vitro differentiated human RBCs. In addition, RBC deformability can be analyzed using micropipette assays.

Method of Deriving and Growing Human ESRE and Culturing of Human Erythroblasts

During murine embryogenesis, sequential waves of primitive and definitive erythroid progenitors emerge in the yolk sac to provide needed RBCs before a permanent hematopoietic stem cell-derived blood system is established. Studies in human embryos indicate that primitive and definitive erythroid lineages similarly emerge in the yolk sac. Without wishing to be bound by any particular theory, it is believed that ESCs recapitulate the early hematopoietic ontogeny found in mammalian embryos. Definitive erythroid progenitors in the yolk sac and in ESCs serve as the source of ESREs.

Figure 4E:
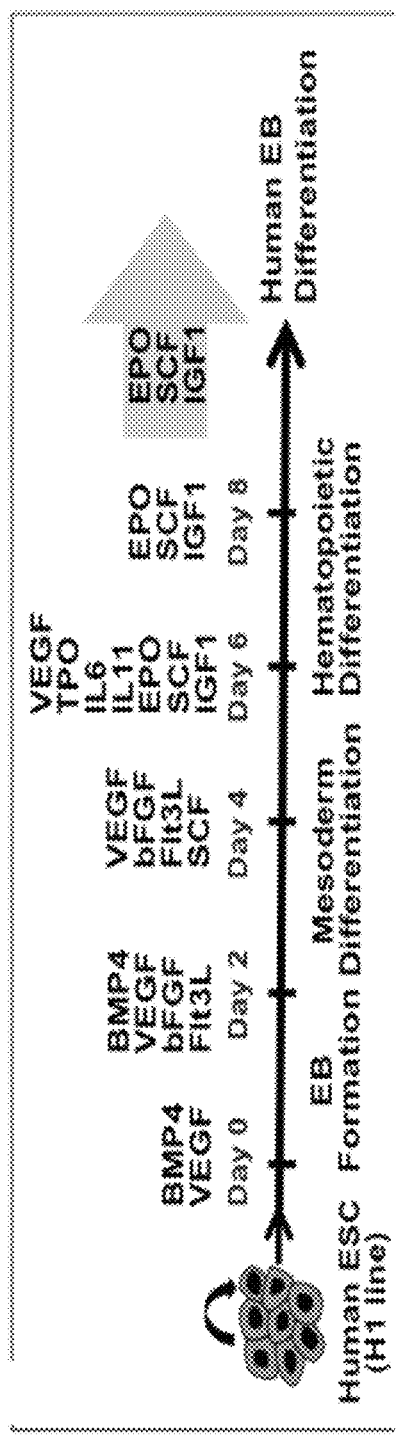

Experiments were designed to test the hypothesis that definitive erythroid progenitors emerging from hESCs can be distinguished from primitive erythroid progenitors by differential gene expression and cell morphology. For example, a representative serum-free hESC differentiation protocol used in the experiments is outlined in FIG. 4E, which indicates that two waves of erythroid progenitors emerge in H1 hESCs (FIG. 4A). Erythroid progenitors from the first wave emerge at days 6-15 of embryoid body (EB) culture and generate colonies of RBCs expressing predominantly embryonic (epsilon) globin, but not Nr3c1 (FIG. 4C), consistent with a primitive erythroid identity. In contrast, colonies derived from the second wave, after day 16, predominantly express fetal (gamma) globin and express Nr3c1 (FIG. 4C), consistent with a definitive erythroid identity.

The two waves of erythroid progenitors emerging from hESCs/EBs can be characterized using clonal colony assays in methylcellulose. The morphology and gene expression of the cells composing individual colonies can also be analyzed. Examples of candidate genes that may help to distinguish primitive and definitive erythroid progenitors include but are not limited to the following genes depicted in Table 2.

TABLE 2

| candidate genes: | |
| --- | --- |
| Primitive erythroblasts | Definitive erythroblasts |
| Hspb8 | Nr3c1 |
| Csf2rb | Sox6 |
| Arid3a | Ca1 |
| Hspal2b | CD82 |
| Slc23a2 | Abcb4 |
| Prkag2 | Itga4 |
| Spns2 | Mppe1 |
| Tatdn3 | Ppap2a |
| Aqp8 | Myb |
| Foxh1 | |

This protocol can also be applied to delineate the kinetics of primitive and definitive erythroid progenitor emergence in several other NIH-approved hESC lines, as well as human iPSC lines, to determine the reproducibility and timing of definitive erythroid progenitor emergence.

Without wishing to be bound by any particular theory, it is believed that hESCs/EBs generate overlapping waves of primitive and definitive erythroid progenitors that can be distinguished by differential gene expression and cell morphology. For example, mature primitive erythroblasts are larger and have a smaller nuclear:cytoplasm ratio compared to definitive erythroblasts. It is believed that the kinetics of blood cell emergence in different hESC lines varies but that the sequential emergence of two waves of erythroid progenitors is conserved.

Figures 4F, 4G, 4H:
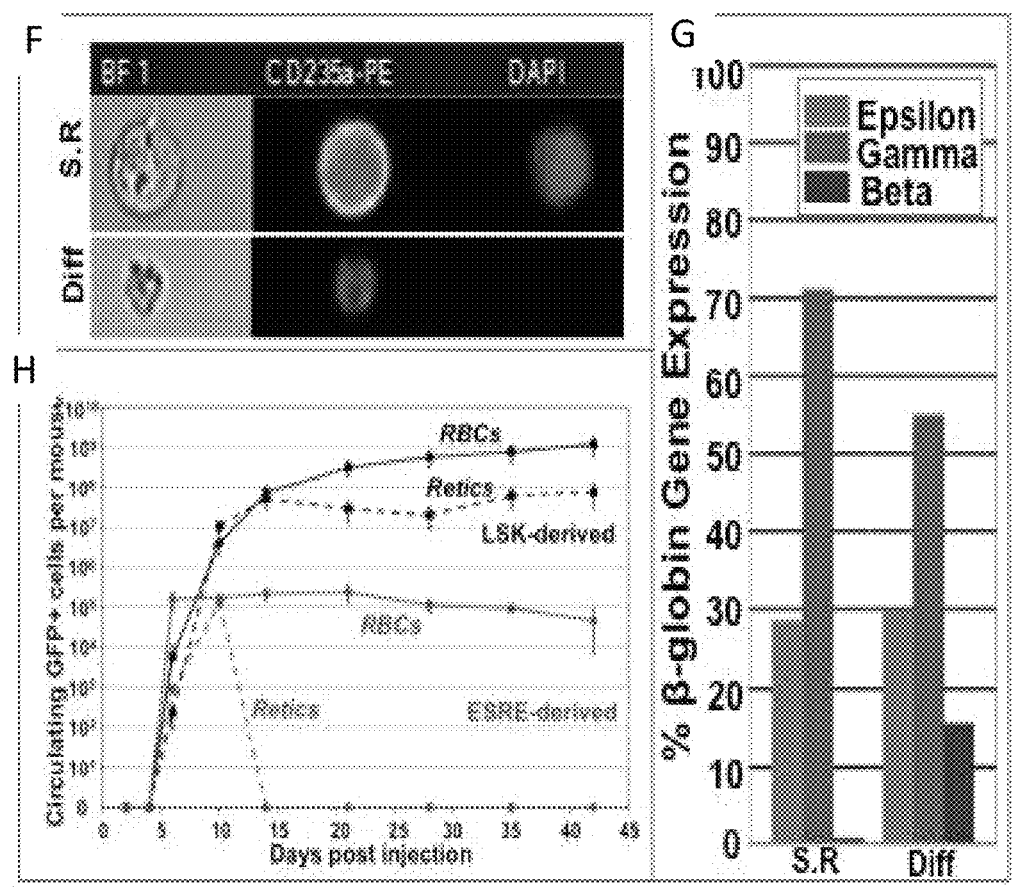

Differentiated hEBs derived from hESCs containing definitive erythroid progenitors serve as a source of human ESREs. The results presented herein provide evidence that definitive erythroid progenitors emerge in H1 hESCs/EBs after day 16 of differentiation (FIG. 4B, 4C). Serum-free self-renewing erythroblast cultures (EPO, SCF, Dex) were initiated with cells from day 16 hESCs/EBs. These initial cultures led to the outgrowth of homogeneous populations of erythroblasts that continue to self-renew for 24-30 days. Flow cytometry was used to visualize and quantify the morphological and immunophenotypic features associated with erythroid precursor maturation. As shown in FIG. 4F, proliferating erythroblasts are large, immature cells with a large nucleus (top panel). These cells express predominantly fetal (gamma) globin (FIG. 4G), consisting with a "definitive" erythroid identity. Differentiation of these self-renewing erythroblasts in maturation media (EPO, serum) resulted in small enucleated RBCs (FIG. 4F, bottom panel) that have up-regulated the expression of the adult (beta) globin gene (FIG. 4G).

It has been found that mouse ESREs can differentiate into RBCs in vivo. Transfusion of GFP+ ESRE results in a transient wave of reticulocytes (young RBCs) followed by a population of mature RBCs that persisted in the circulation >40 days (FIG. 4H). These data support the concepts that ESREs 1) are not malignant, 2) can fully mature in vivo over 5-6 days, and 3) can generate normal RBCs with a long functional lifespan in the circulation.

Erythroblasts derived from hESCs/EBs are cultured in conditions that support their extensive self-renewal. Various glucocorticoid receptor (GR) agonists, which activate GR and block erythroid maturation, are tested for their ability to promote extensive human erythroblast self-renewal. Cell viability (trypan stain), erythroid maturation (benzidine stain), and cell morphology (Giemsa stain) of cultured erythroblasts can be quantified. Erythroblast cultures derived from human cord blood can serve as a "negative" control, since these cells only self-renew for about 15 days. Human self-renewing erythroblasts are differentiated in vitro using stromal co-culture are analyzed for hemoglobin content, oxygen binding affinity, and RBC deformability using laser diffraction. The in vivo function of human RBCs can be tested in immunocompromised (NSG) mice, tracking the cells with human-specific erythroid marker CD235.

Without wishing to be bound by any particular theory, it is believed that optimization of the culture conditions promote the extensive self-renewal of hESC-derived, but not of cord blood-derived, human erythroblasts. Since ESREs have been generated from p53-null fetal and adult mice, knocking down p53 in human cord blood-, or bone marrow-, derived erythroblasts is an alternative approach to generate human ESREs. It is also expected that these human erythroblasts, like their adult counterparts, are able to differentiate into enucleated RBCs in vitro and function in vivo in an animal model.

ESREs Derived from Human Embryonic Stem Cells Differentiated In Vitro

Human ESCs (WA01) were enzymatically (using Collagenase IV, Stem Cell Technologies) and mechanically (using a cell scraper) dissociated into small clumps of cells. In some instances, H1 human embryonic stem cells (WA01) were dissociated and cultured in serum-free medium sequentially, as indicated in Table 1, in a hypoxic environment (5% $O_2$). Human embryonic stem cells initially form embryoid bodies (EB) and continually differentiate toward hematopoietic lineages. From day 6 of EB differentiation, hematopoietic cells were released into suspension, and these cells were harvested for subsequent erythroblast expansion cultures.

Figure 4I:
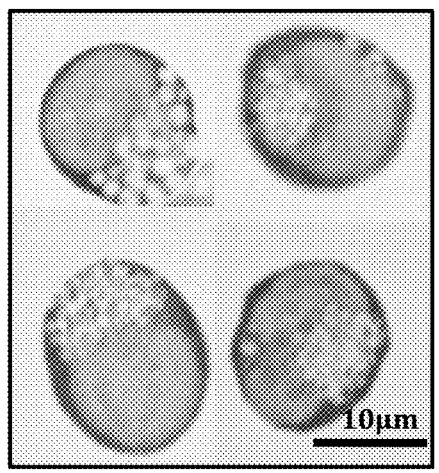

Erythroblast expansion cultures were maintained under conditions discussed elsewhere herein, including stem cell factor, erythropoietin and dexamethasone. Several different media were tested for their ability to sustain the continued self-renewal of human erythroblasts. While three of the four different media that were tested (StemSpan (Stem Cell Technologies), StemSpan SFEM-II (Stem Cell Technologies, and QBSF60 (Quality Biologicals) supported the proliferative expansion of the erythroblasts for 10-15 days, one of the four media (StemSpan-ACF (Stem Cell Technologies)) resulted in the continuous proliferation of erythroblasts for 50 days. The morphology of the proliferating erythroblasts (at day 36 of expansion) is shown in FIG. 4I. These cells have the classic appearance of proerythroblasts with a high nuclear:cytoplasmic ratio, open chromatin with nuclei, and deeply basophilic cytoplasm. The proliferative expansion of these cells is consistent with an ESRE identity. Placement of these cells in differentiation medium resulted in the maturation of late stage erythroblasts and enucleated red cells.

In one experiment, erythroblasts released from day 38 human H1 embryoid bodies were obtained and erythroblast cultures were initiated. Briefly, released cells from EB differentiation day 38 (WA01, passage #38) were resuspended in a 24-well tissue culture dish in serum-free human erythroid expansion media. This media includes StemSpan™-ACF (Stem Cell Technologies) supplemented with 2 U/mL human recombinant Epo (Amgen), 100 ng/mL human recombinant SCF (PeproTech), $10^{-6}$M dexamethasone (Sigma), 40 ng/mL human recombinant insulin-like growth factor-1 (PeproTech), 0.4% lipid mixture EX-CYTE (Millipore), and penicillin/streptomycin (Invitrogen). Expansion media was freshly prepared every week. Cells were maintained in $\leq 1 \times 10^6$ cells/mL daily by partial medium changes.

The results presented herein show the successful expansion of human erythroblasts through 50 days of continuous culture. This serves as a proof-of-principle that ESREs can be derived from human embryonic stem cells. Based on the results presented herein experiments can be performed to optimize the culture conditions for human erythroblast and to maximize the potential of embryonic erythroblasts to undergo extensive self-renewal.

Unique to this invention disclosure is the concept that ESREs can be specifically derived from the first "definitive" erythroid progenitors that emerge during embryogenesis. Results presented herein provide evidence that ESRE populations can be generated from human embryonic stem cells. Human ESREs can be used to produce large quantities of mature red blood cells in vitro for clinical use.

Example 2: Using ESREs to Screen for Activators of Human Fetal Globin Expression The characteristics of ESREs—rapid proliferation with maintenance of normal ploidy, along with the ability to terminally mature with high efficiency to produce RBCs—provide a number of practical applications. For example ESREs can be derived with stably integrated transgenes or subjected to siRNA knockdowns in order to derive RBCs with artificially engineered protein compositions; moreover, the ability to derive ESREs from ES or iPS cells allows for targeted alterations within endogenous gene loci as well. Such manipulations represent applications of ESRE technology.

In some instances, ESREs are used to perform a high-throughput screen for chemicals capable of influencing the expression of human β-globin genes. β-hemoglobinopathies, which involve either a mutated β-globin gene (as in sickle cell anemia) or significant decreases in adult β-globin gene expression (as in deletion β-thalassemias), represent the most common class of genetically inherited disorders in the world. The effects of mutant alleles, however, are readily reversed by expression of a normal β-globin gene—for example, heterozygosity for hemoglobin S is almost always a benign condition, while a mouse model of sickle cell anemia has been used to demonstrate that symptoms are alleviated or eliminated upon overexpression of normal β-globins (Levasseur et al., 2003, Blood 102:4312-4319). A clinical pathway toward providing for expression of normal β-globins originates from the fact that expression from within the β-globin gene cluster is developmentally regulated. The embryonic ε-globin and fetal γ-globin genes are silenced in the adult, but can potentially be re-activated. To a limited extent, such "re-activation" therapy is currently in use, and there are a number of drugs available that accomplish modest elevations in γ-globin expression levels in adult patients (Bauer et al., 2012, Blood 120:2945-2953).

A high-throughput chemical screen for compounds that upregulate human fetal γ-globin gene expression in ESREs can be performed. ESREs, which harbor an artificially engineered human β-globin locus can be used. In this transgene, the fetal Aγ-globin gene is replaced with the coding sequence for firefly luciferase (Luc), while the adult β-globin gene has been replaced with the coding sequence for Renilla luciferase (Ren). These gene replacements provide a convenient readout for expression driven by the corresponding γ- and β-globin control sequences, and can be used in high-throughput fluorimetric assays. ESREs harboring the altered human transgene can be generated from embryonic erythroid tissue derived from matings of these mice.

In addition to initiating the process of developing new drugs capable of elevating fetal γ-globin levels and thus alleviating multiple β-hemoglobinopathies, this approach serves as a proof-of-principle that the ESRE system can be used for high-throughput screening for new therapies for disorders of RBC production and function.

Example 3: p53 Biology and Extensive Erythroid Self-Renewal

Figure 5:
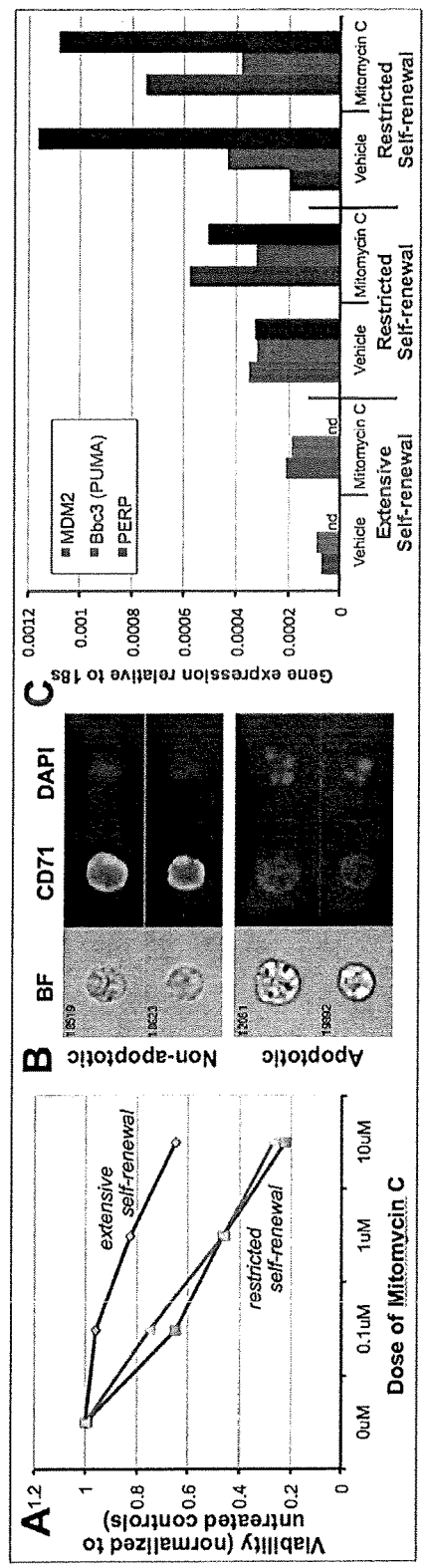
FIG. 5, comprising
Figure 6:
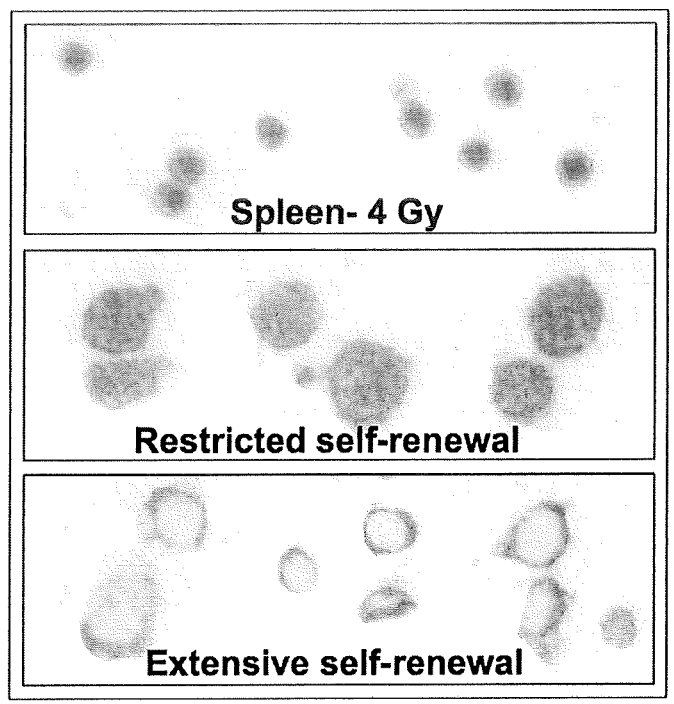
FIG. 6 is an image depicting immunohistochemical localization of p53 protein. Upper panel: p53 in irradiated mouse spleen cells is predominantly nuclear. Middle panel: p53 in erythroblasts undergoing restricted self-renewal is both cytoplasmic and nuclear. Lower panel: p53 in erythroblasts undergoing extensive self-renewal is predominantly cytoplasmic.

Experiments were conducted to determine if p53 is differentially regulated in erythroblasts undergoing restricted versus extensive self-renewal. Murine erythroblasts with restricted self-renewal, cultured from adult marrow and late fetal liver and analyzed at 6-9 days of culture, were compared to ESREs derived from E10.5 yolk sac and continuously cultured for 199 days. Both the restricted and extensively self-renewing erythroblast populations were proliferating at the same rate, doubling in numbers daily. The cultured erythroblasts were subjected to genotoxic injury using mitomycin C added to the cultures for 14 hours. As shown in FIG. 5A, ESREs were more viable than restricted self-renewing cultures at all tested concentrations of mitomycin C. Rates of apoptosis were quantified using imaging flow cytometry to identify erythroblasts with nuclear blebbing (FIG. 5B). At all concentrations of mitomycin C, the rates of apoptosis were markedly lower in ESREs than cells undergoing restricted self-renewal, e.g., at the 0.1 uM dose of mitomycin C, the rate of apoptosis was 17% in ESREs and 52% and 62% for the cultures undergoing restricted self-renewal. Furthermore, the mRNA expression of several p53-target genes was quantitated by qPCR. Mitomycin C exposure was associated with the upregulation of Mdm2 in all the cultures and of PUMA only in the ESREs (FIG. 5C, blue and red bars, respectively). Of note, the apoptotic effector PERP was not expressed by ESREs either during their steady-state proliferation or following mitomycin C exposure (FIG. 5C, black bars).

p53 in control irradiated mouse spleen cells is predominantly nuclear (FIG. 6, upper panel). p53 is present in both cytoplasm and nucleus in erythroblasts undergoing restricted self-renewal (FIG. 6, middle panel). In marked contrast, p53 is predominantly cytoplasmic in ESREs (FIG. 6, lower panel). Taken together with the data in FIG. 5, it is believed that p53 is differentially regulated in erythroblasts undergoing extensive versus restricted self-renewal. Accordingly, experiments can be designed to test the hypothesis that p53 function is down-regulated in ESREs, which contributes to their extensive self-renewal capacity.

Delineate the Function of p53 in Wild-Type and p53-Null Erythroblasts Undergoing Restricted Versus Extensive Self-Renewal.

A better understanding of the mechanism of p53 function provides insights into the regulation of erythroid precursor self-renewal and identifies p53 as a potential target to facilitate the generation of ESREs from cord blood or adult peripheral blood mononuclear cells. The results provide evidence that ESREs are more tolerant of genotoxic stress (FIG. 5A), and that p53 itself, and the pathways downstream of p53, are differentially regulated in erythroblasts undergoing extensive versus restricted self-renewal (FIG. 6; 5C). While no significant differences in p53, MDM2 or MDM4 mRNA levels have been found in murine versus erythroblasts undergoing restricted versus extensive self-renewal, the post-translational regulation of p53 appears to be dramatically different.

Experiments are performed to confirm the differential response of erythroblasts undergoing restricted versus extensive self-renewal to genotoxic injury, using both mitomycin C, as well as γ-irradiation at 1, 2, and 4 Gy. Cell numbers, viability, apoptosis rates, and cell cycle status are compared to vehicle-treated/unirradiated control erythroblast cultures using imaging flow cytometry. The response to genotoxic stress of self-renewing erythroblasts derived from wild-type, p53+/−, and p53−/− littermates can be analyzed. These experiments are conducted during the restricted phase of erythroblast expansion, i.e., during the first 2 weeks of culture. Changes in the rates of proliferation, propensity to generate extensive self-renewing cultures, and response to genotoxic stress in p53+/− erythroblasts provides further evidence for a role in p53 regulation of these processes. Without wishing to be bound by any particular theory, it is believed that the lack of p53 in human cells does not interfere with erythroid maturation.

The Ability of p53 Loss-of-Function to Promote ESRE Generation from Human Cord Blood.

ShRNA-containing lentiviral vectors (OpenBiosystems) can be used to knock-down p53 in adult-derived self-renewing erythroblasts to endow them with extensive self-renewal capacity. Erythroblast cultures with various degrees of p53 knock-down, analyzed by qPCR and western blots, can be tested for their capacity to extensively self-renew. Lentiviral knockdown of gene expression in ESREs can achieve 20%-95% gene knock-down in erythroblasts undergoing self-renewal in EPO, SCF, and dexamethasone. Importantly, puromycin selection does interfere with self-renewal capacity.

Experiments can be conducted to knock-down p53 in self-renewing human erythroblasts derived from cord blood, which undergo restricted self-renewal for 10-15 days. Several shRNA-containing lentiviral vectors (OpenBiosystems) can be individually introduced into the erythroblasts within 2-4 days after initiating the cultures. The degree of p53 knock-down can be analyzed by qPCR and western blot and the most effective sequences subsequently used.

Without wishing to be bound by any particular theory, it is believed that p53 is differentially regulated in human erythroblasts undergoing extensive versus restricted self-renewal and that attenuated p53 function is associated with, and contributes to, extensive erythroblast self-renewal. Given the panoply of downstream p53 effects on cell survival, cell division, differentiation, and senescence, it is unlikely that down-regulation of PERP alone, which would be expected to specifically alter apoptosis, would prove more effective in expanding self-renewal capacity when compared with knockdown of p53.

The present invention relates to the generation of human erythroblasts with extensive self-renewal capacity. The ESREs of the invention can be used to generate a differentiated cell product and can be used in the clinic, particularly issues of scale, since a unit of blood contains $2.5\times10^{12}$ RBCs. In some instances, it is desirable to use bioreactors for ESRE expansion and differentiation. The invention provides compositions and methods to produce a limitless source of RBCs. The ability to generate ESREs from adult tissues lays the foundation for individualized blood cell therapeutics. In addition, the cells of the invention allows for the creation of in vitro models of erythroid-specific diseases such as hemoglobinopathies, cytoskeletal disorders, and RBC enzymopathies.

Example 4: Bmi-1 is a Central Regulator of Erythroid Self-Renewal

The results presented herein demonstrate that Bmi-1 is a central regulator of erythroid self-renewal. Gain-of-function experiments were performed to express Bmi-1 in human fetal liver cells. Experiments were also designed to express Bmi-1 in bone marrow-derived cells.

Figure 7:
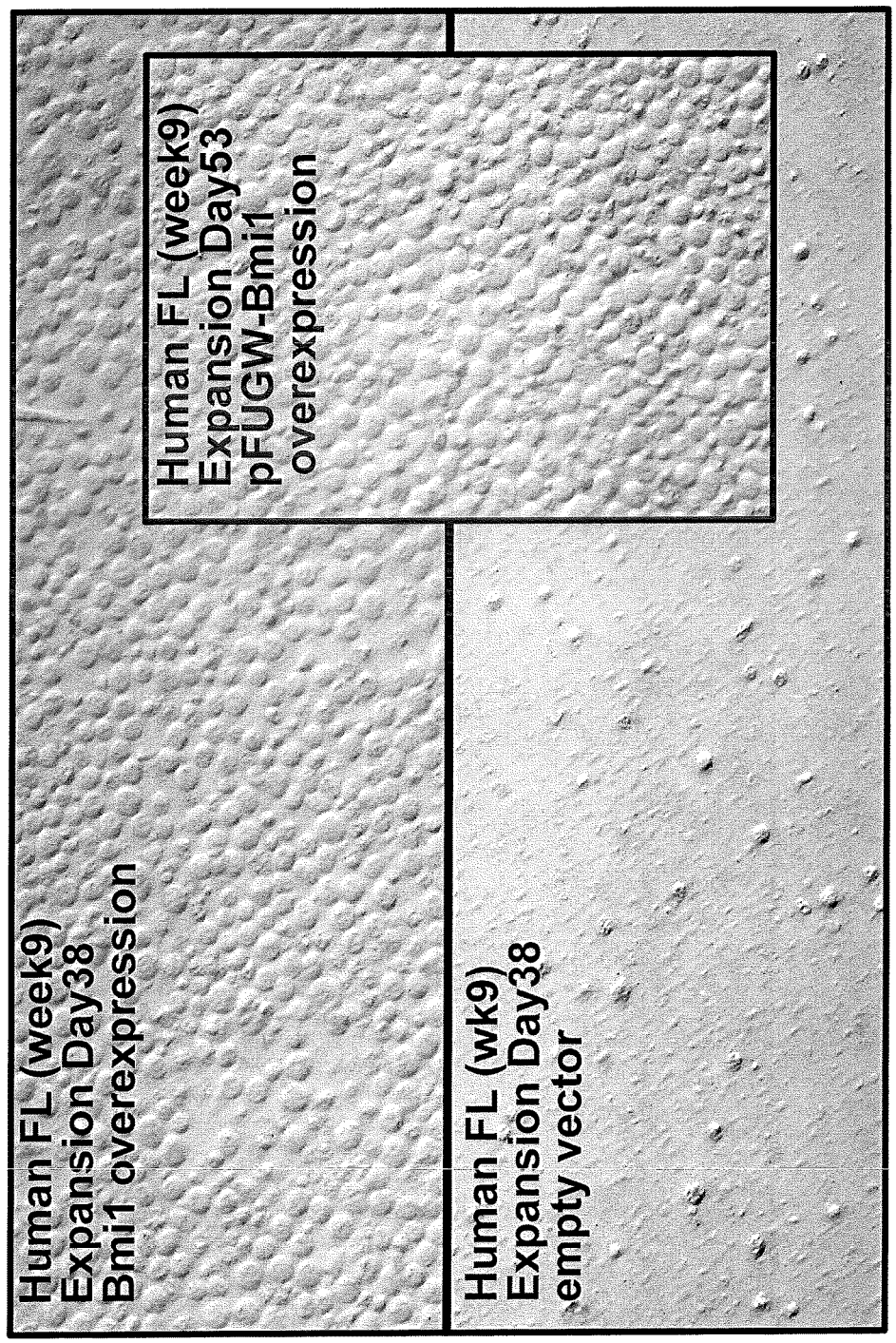
FIG. 7 is an image demonstrating that human fetal liver cells that overexpress Bmi-1 continued to proliferate for more than 75 days.
Figure 8:
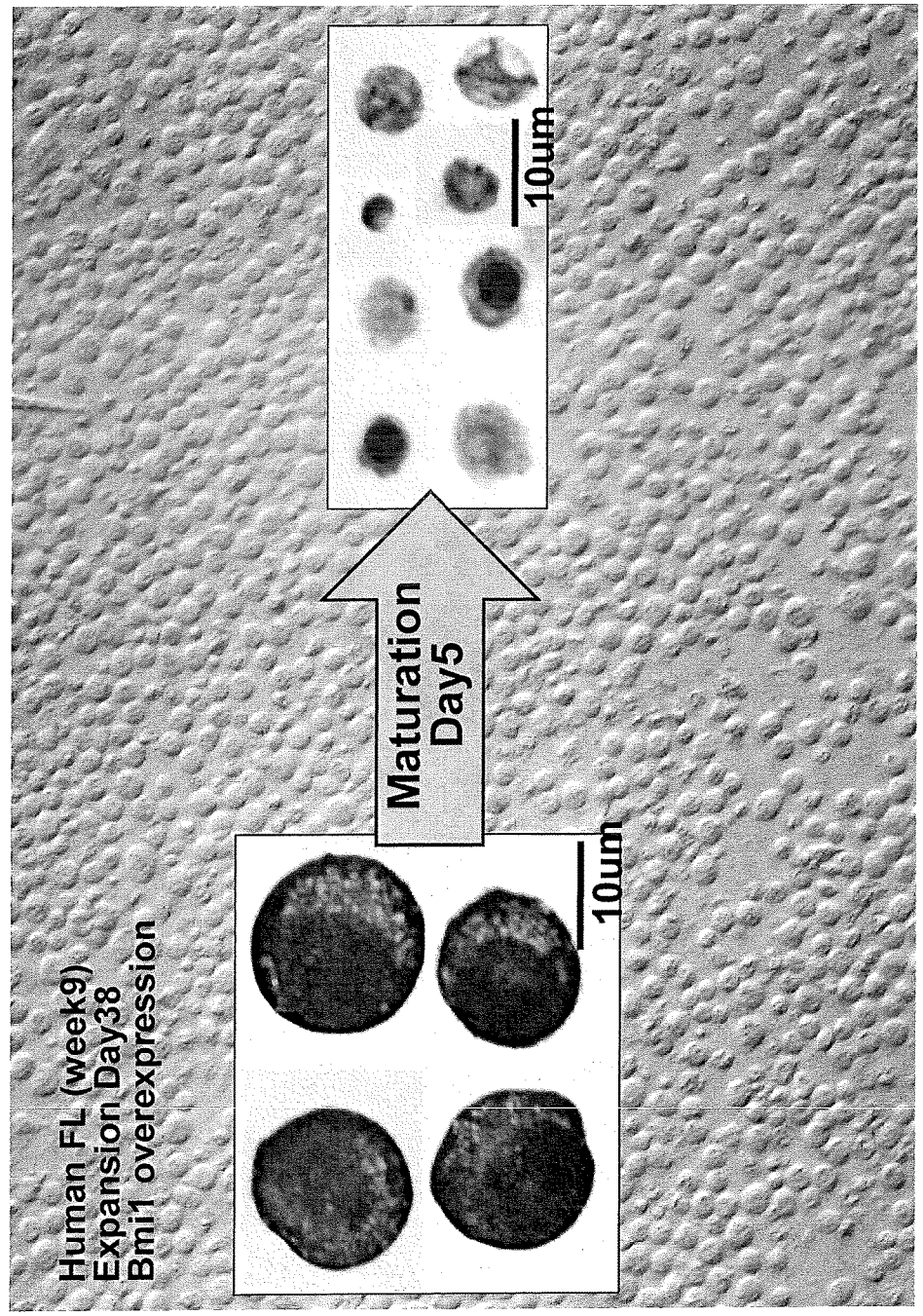
FIG. 8 is an image depicting the maturation of the expanded human fetal liver cells that overexpress Bmi-1 into late-stage erythroblasts and even enucleate to form reticulocytes.
Figure 9:
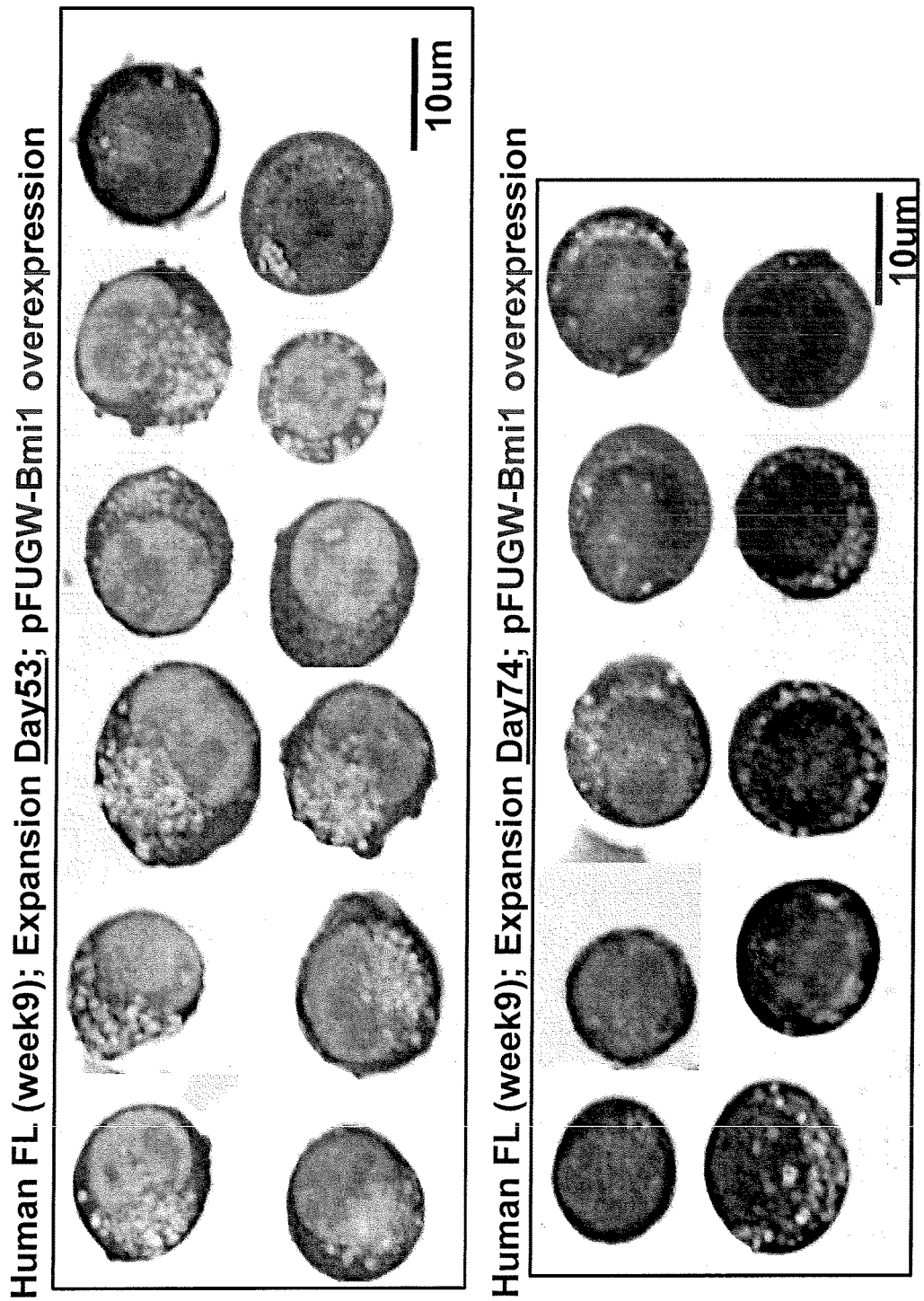
FIG. 9 is an image showing examples of human erythroblasts from the culture containing Bmi-1 overexpressing cells.

Briefly, 9 week human fetal liver cells were dissociated and cultured with expansion media. After 6 days of expansion, human cells were infected with a lentivirus containing murine Bmi-1 in the FUGW backbone (Addgene). Cells infected with empty vector ceased proliferating by Expansion Day 38, while cells infected with Bmi-1 overexpression continued to proliferate (bright field picture) for more than 75 days (FIG. 7). These proliferating cells have the morphology of immature erythroblasts (Giemsa staining). When placed in erythroid maturation media for 5 days, these immature erythroblasts matured to late-stage erythroblasts and even enucleate to form reticulocytes (FIG. 8). FIG. 9 shows examples of human erythroblasts from the culture containing Bmi-1 over-expansion.

Example 5: Lipid Supplementation and Erythroblast Self-Renewal

Figure 10:
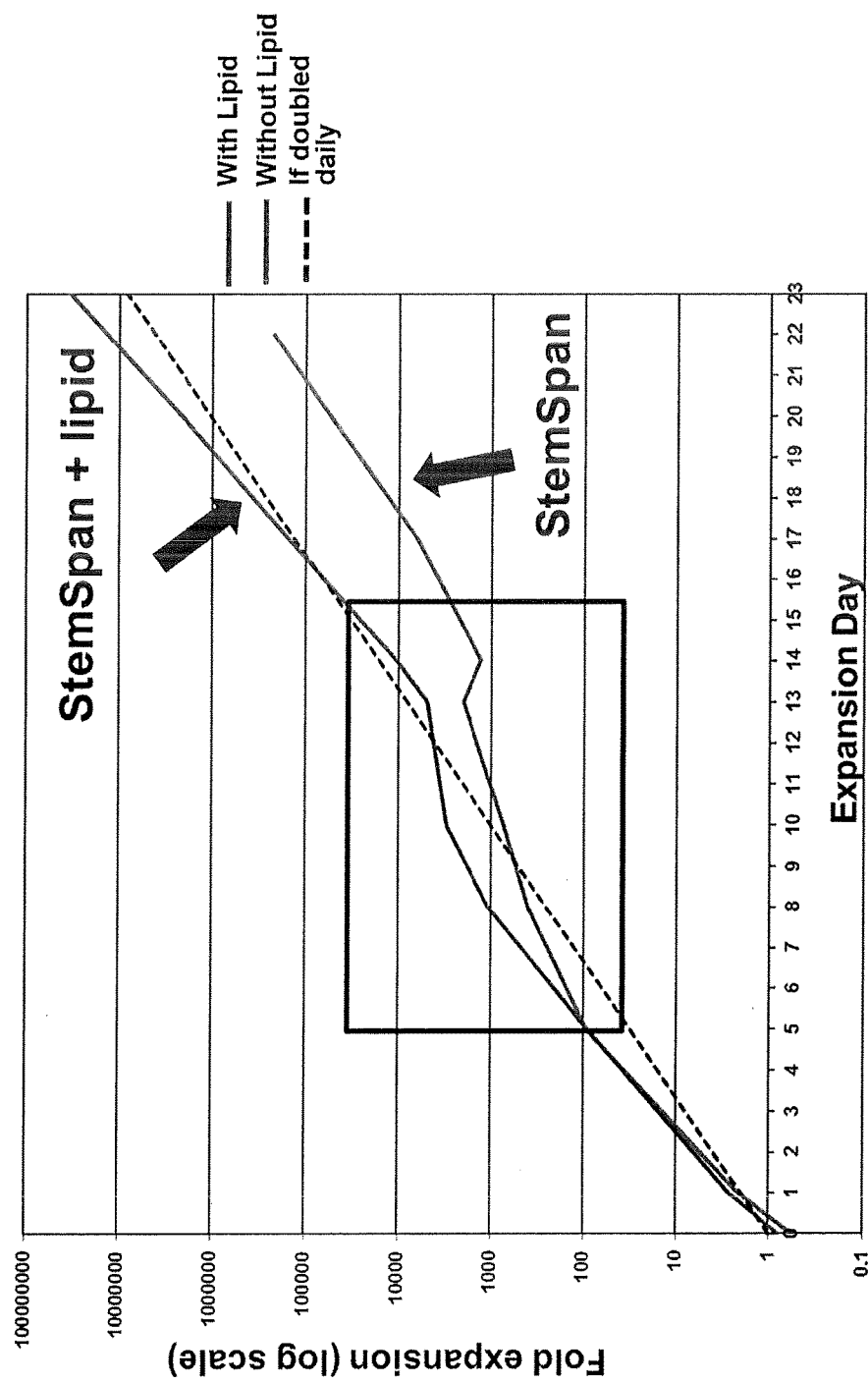
FIG. 10 is a chart showing that withdrawal of lipid supplements from the StemSpan expansion media slowed down erythroblast proliferation.
Figure 11:
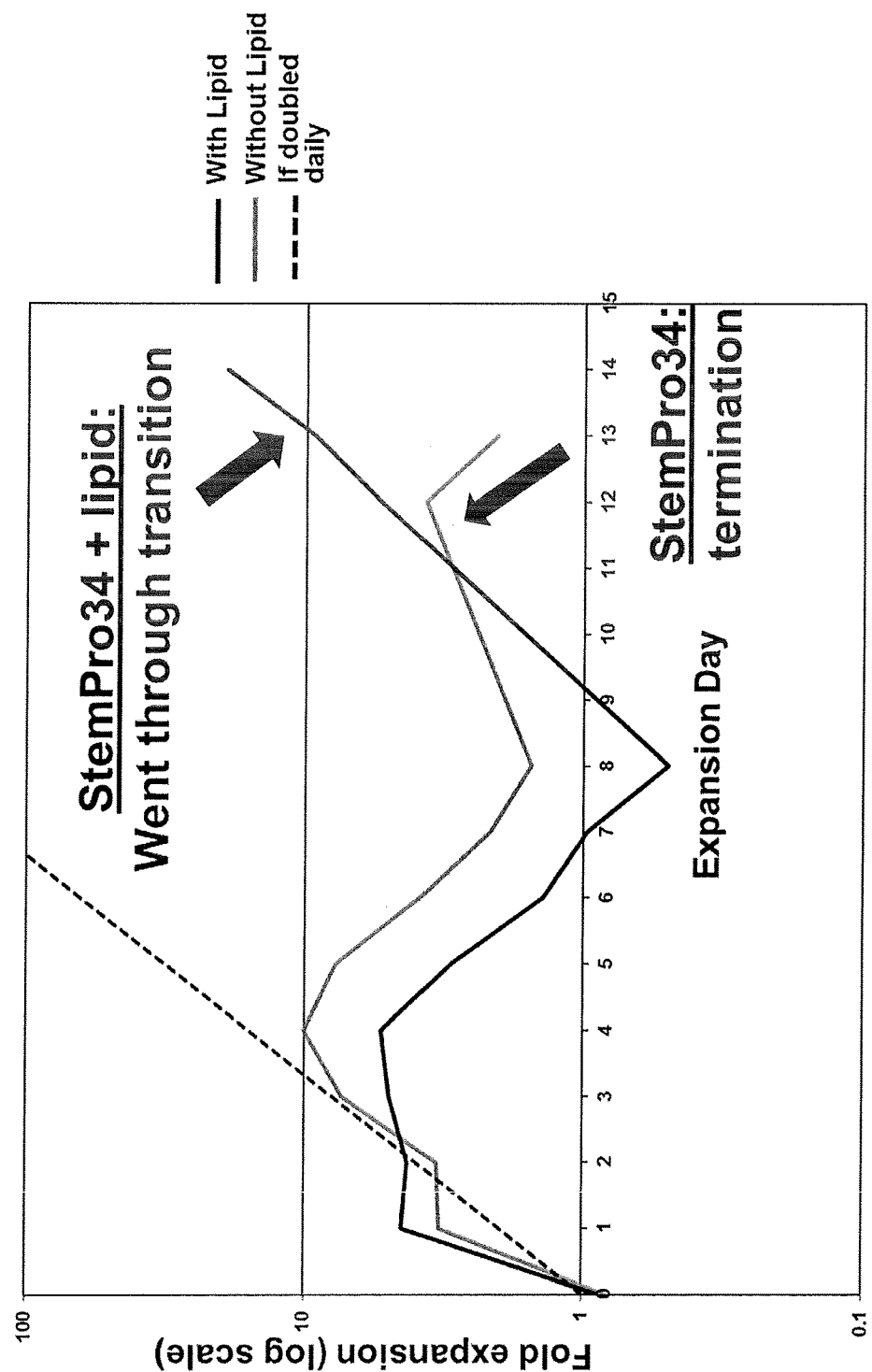
FIG. 11 is a chart showing that withdrawal of lipid supplements from the StemPro34 expansion media blocked the ability of erythroblasts undergoing restricted self renew (SREs) to enter the "extensive" phase and become ESREs.
Figure 12:
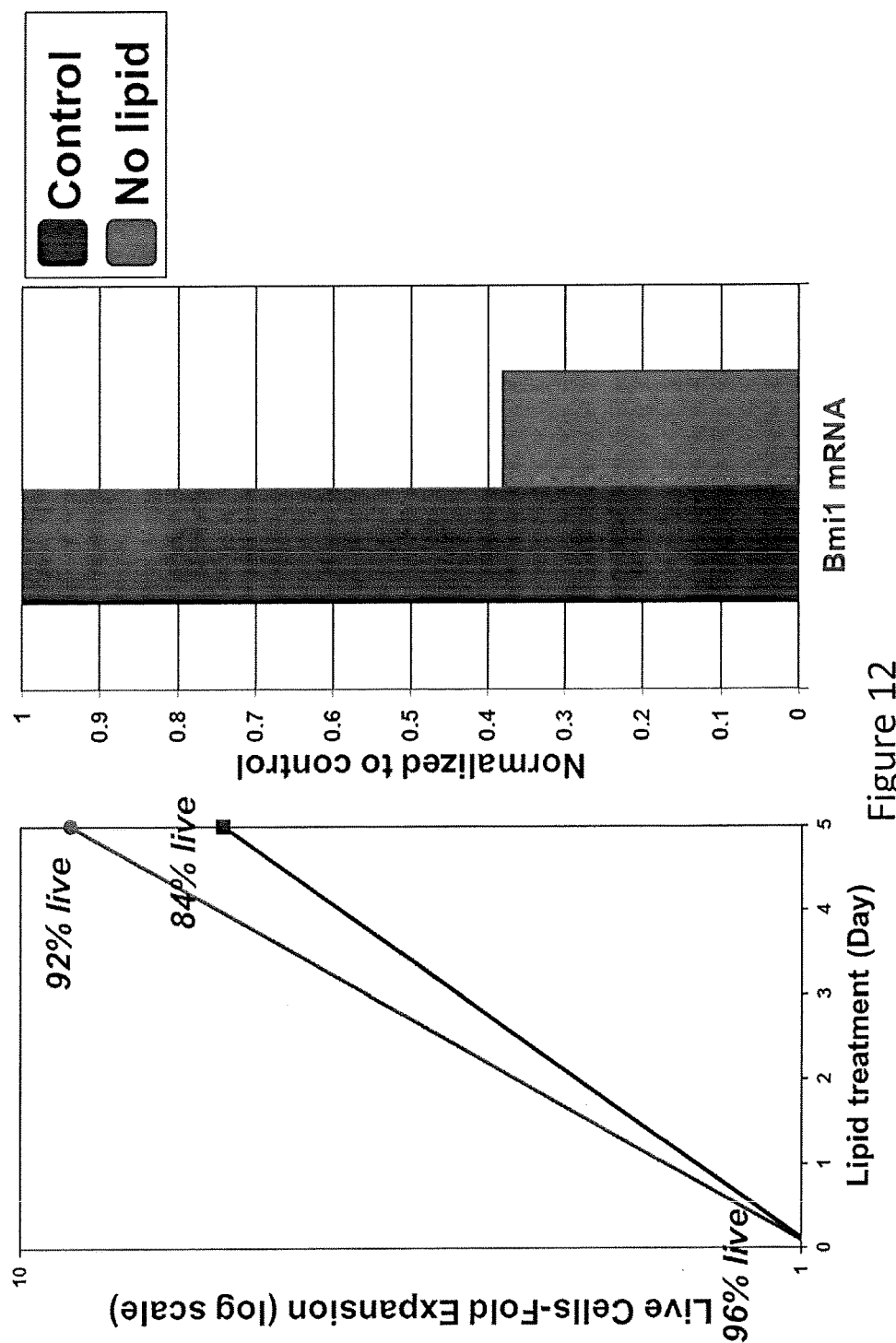
FIG. 12 is a chart showing that when ESREs were cultured with or without lipid supplements for 5 days, Bmi1 transcript levels were reduced in the "no lipid" condition compared to the control culture containing lipids.
Figure 13A:
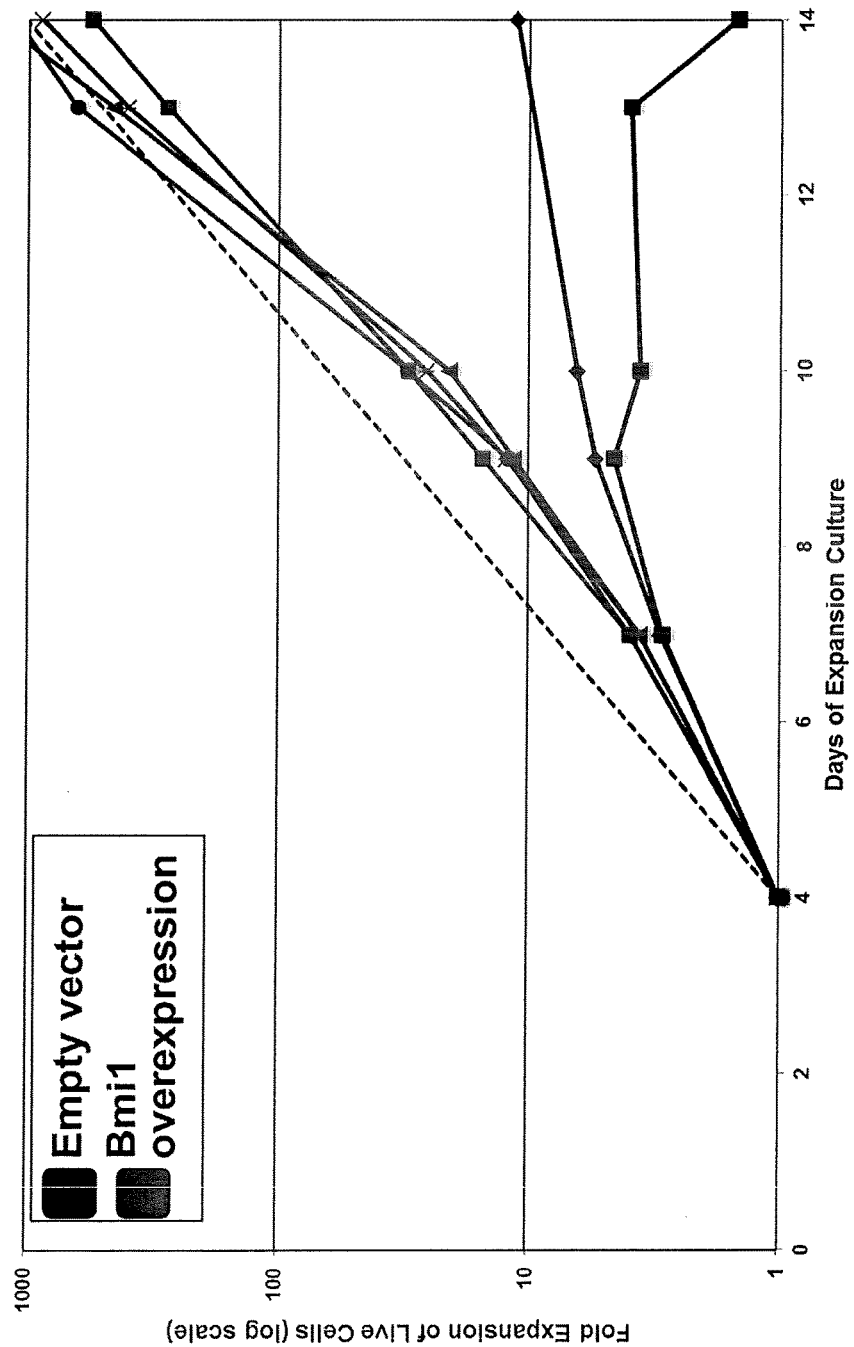
FIGS. 13A and 13B, is a series of charts showing that induced expression of Bmi-1 in adult mouse cells leads to enhanced self-renewal.
Figure 13B:
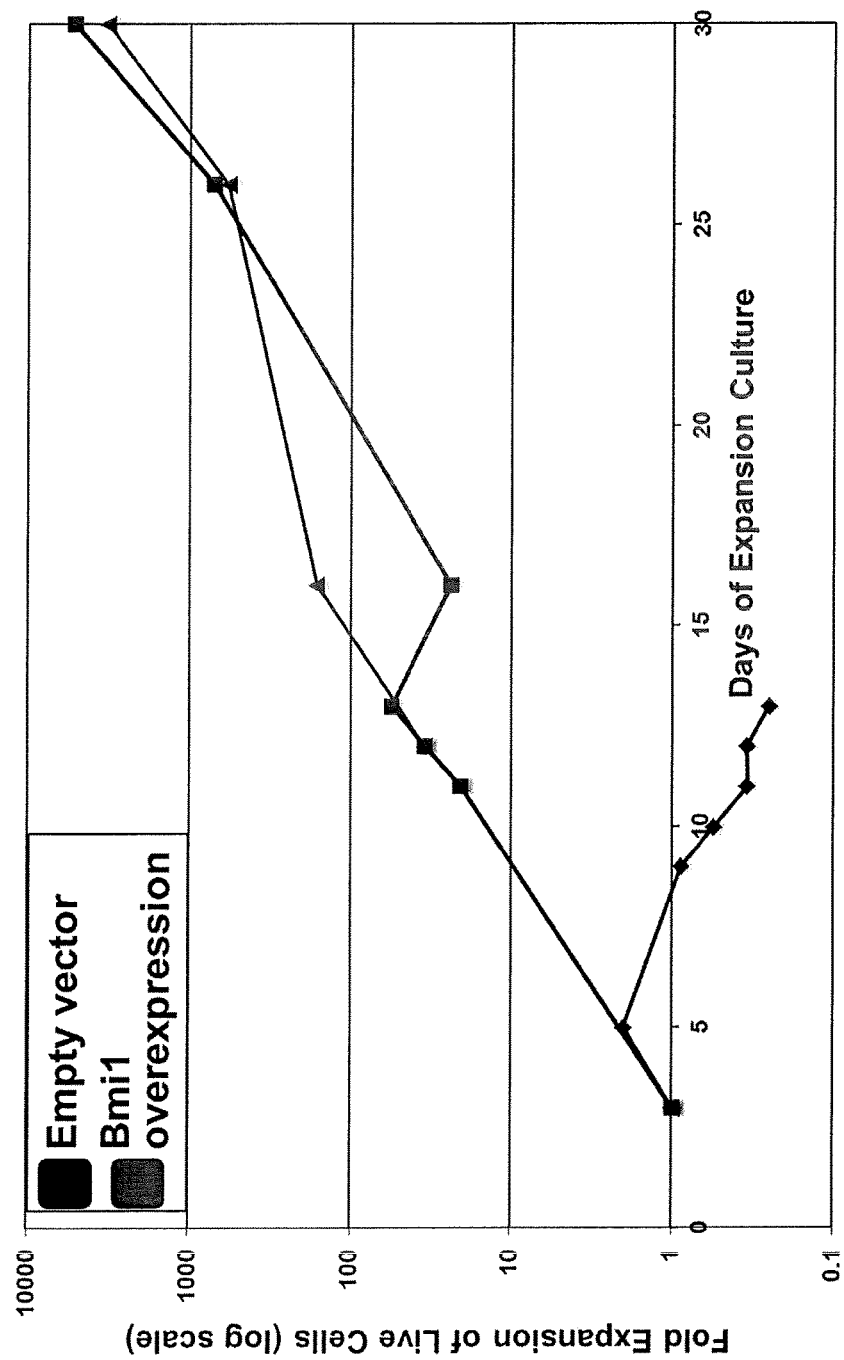
Figure 14:
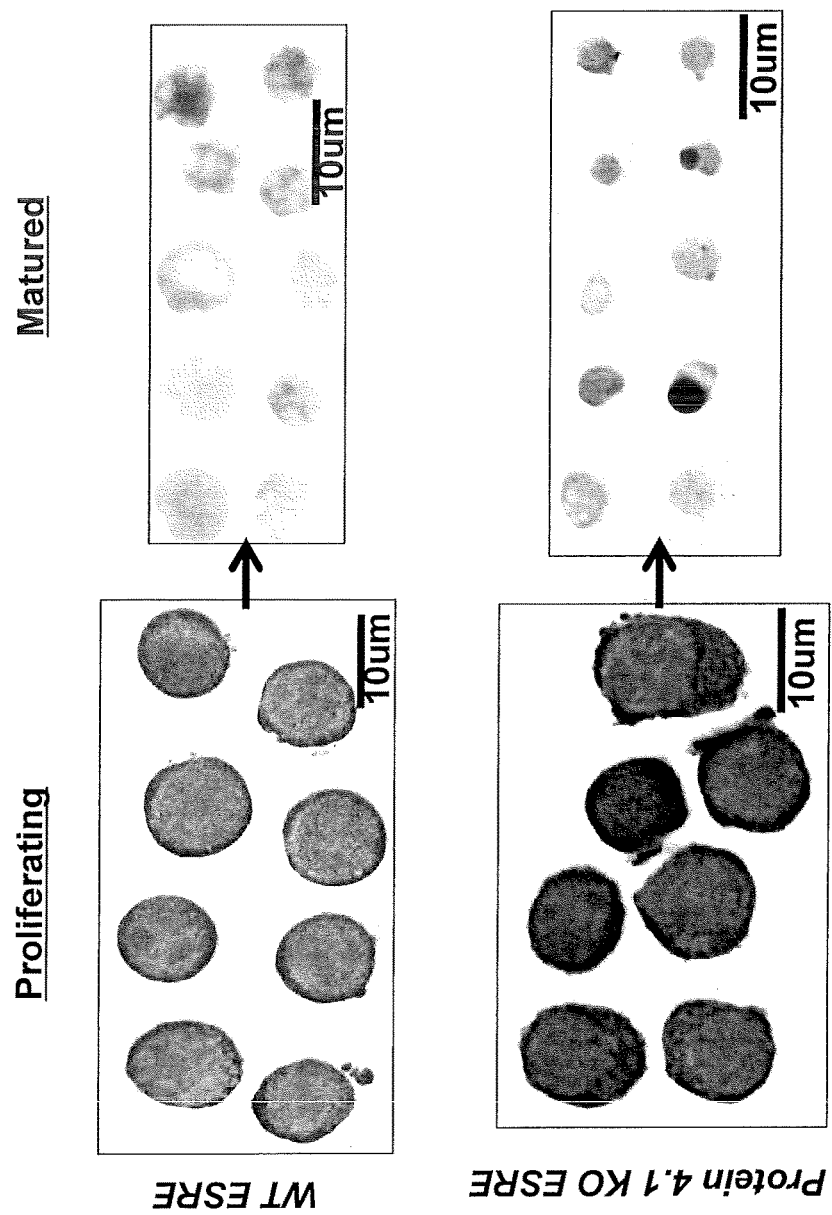
FIG. 14 is a chart showing proliferating cells (Protein 4.1 knockout cells; Expansion Day 16; bottom panel) have the morphology of immature erythroblasts (Giemsa staining). When placed in erythroid maturation media for 3 days, these immature erythroblasts mature to late-stage erythroblasts and even enucleate to form reticulocytes. These data support the concept that ESREs can serve as a model system to study erythroid-specific diseases.
Figure 15:
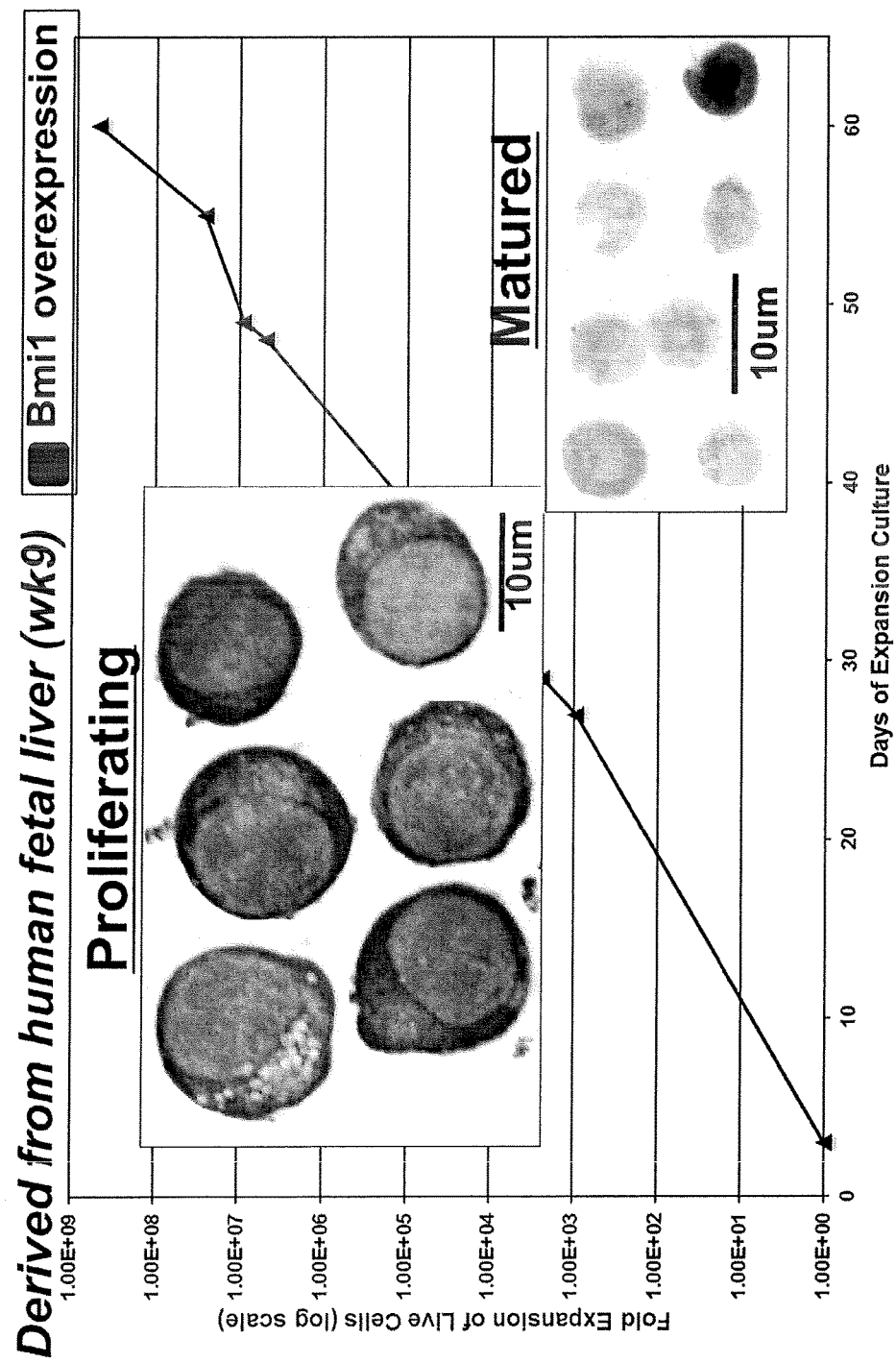
FIG. 15 is a chart showing that induced expression of Bmi-1 in human erythroblasts leads to their extensive self-renewal.
Figure 16A:
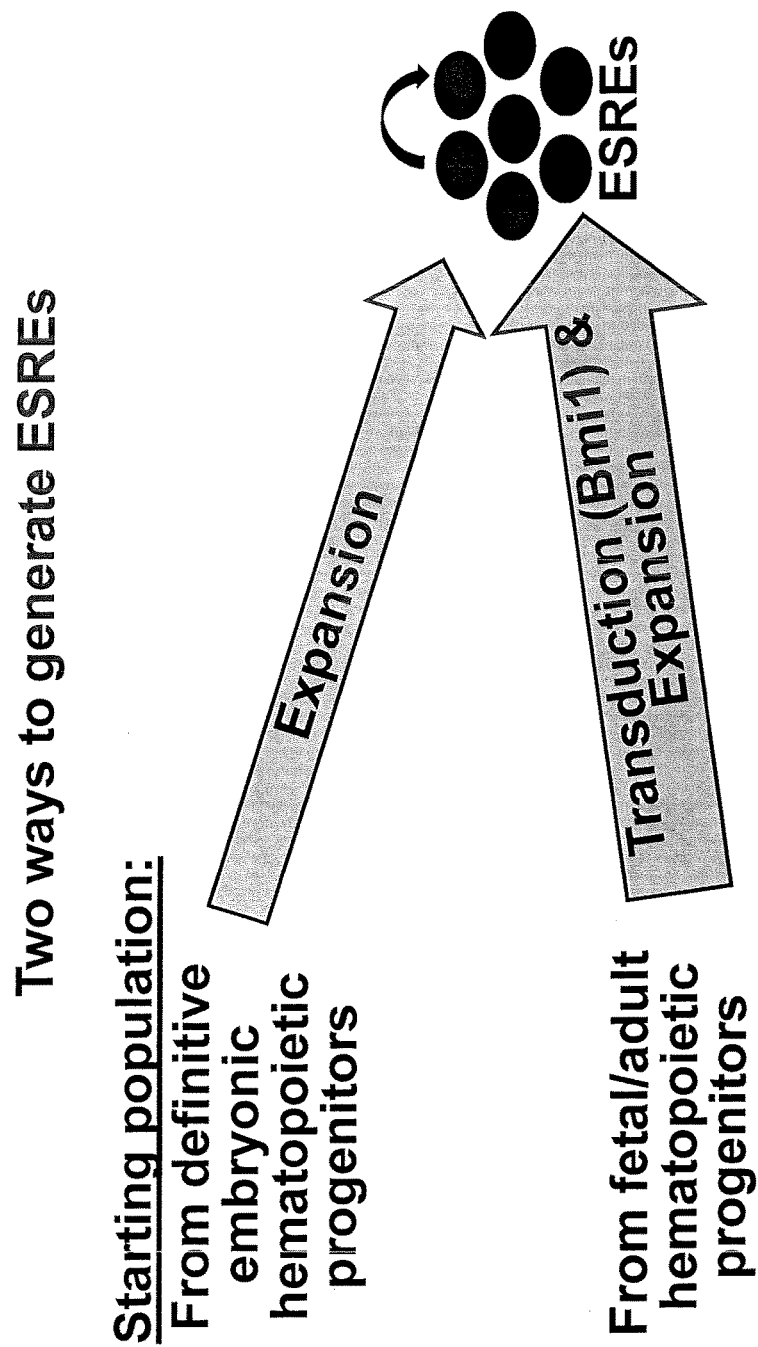
FIGS. 16A through 16C, is a series of schematics demonstrating the generation of ESREs.
Figure 16B:
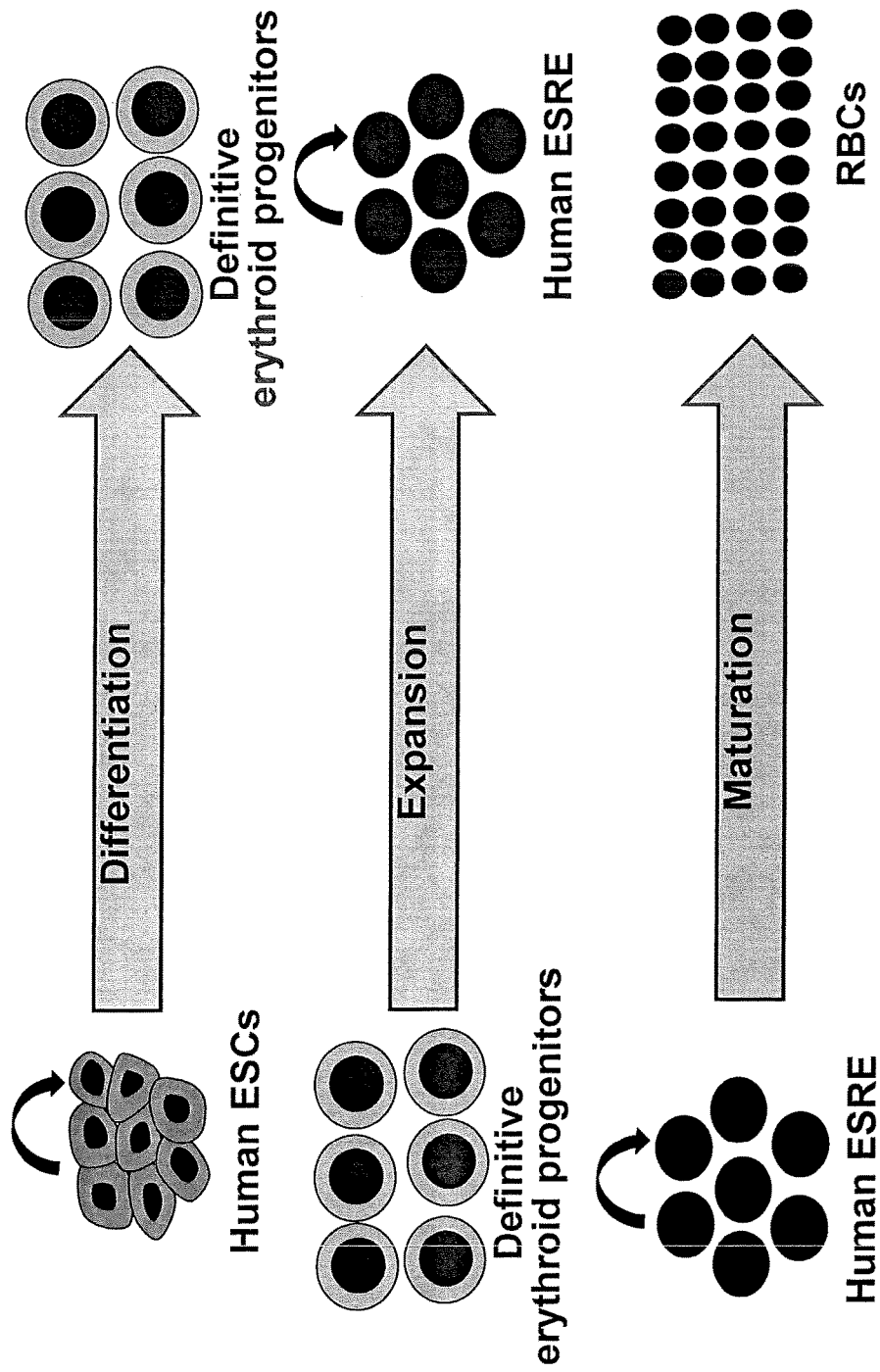
Figure 16C:
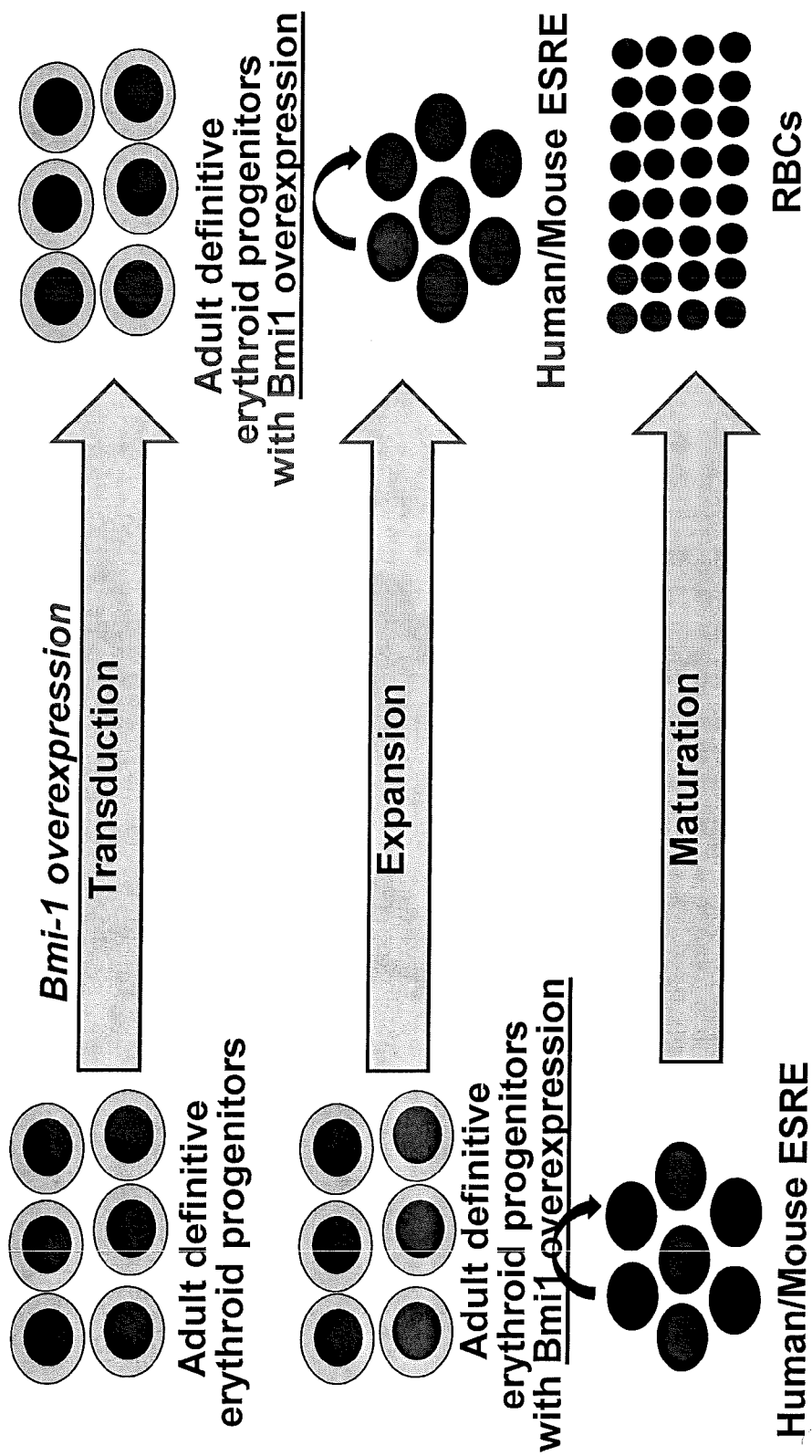
Figure 17:
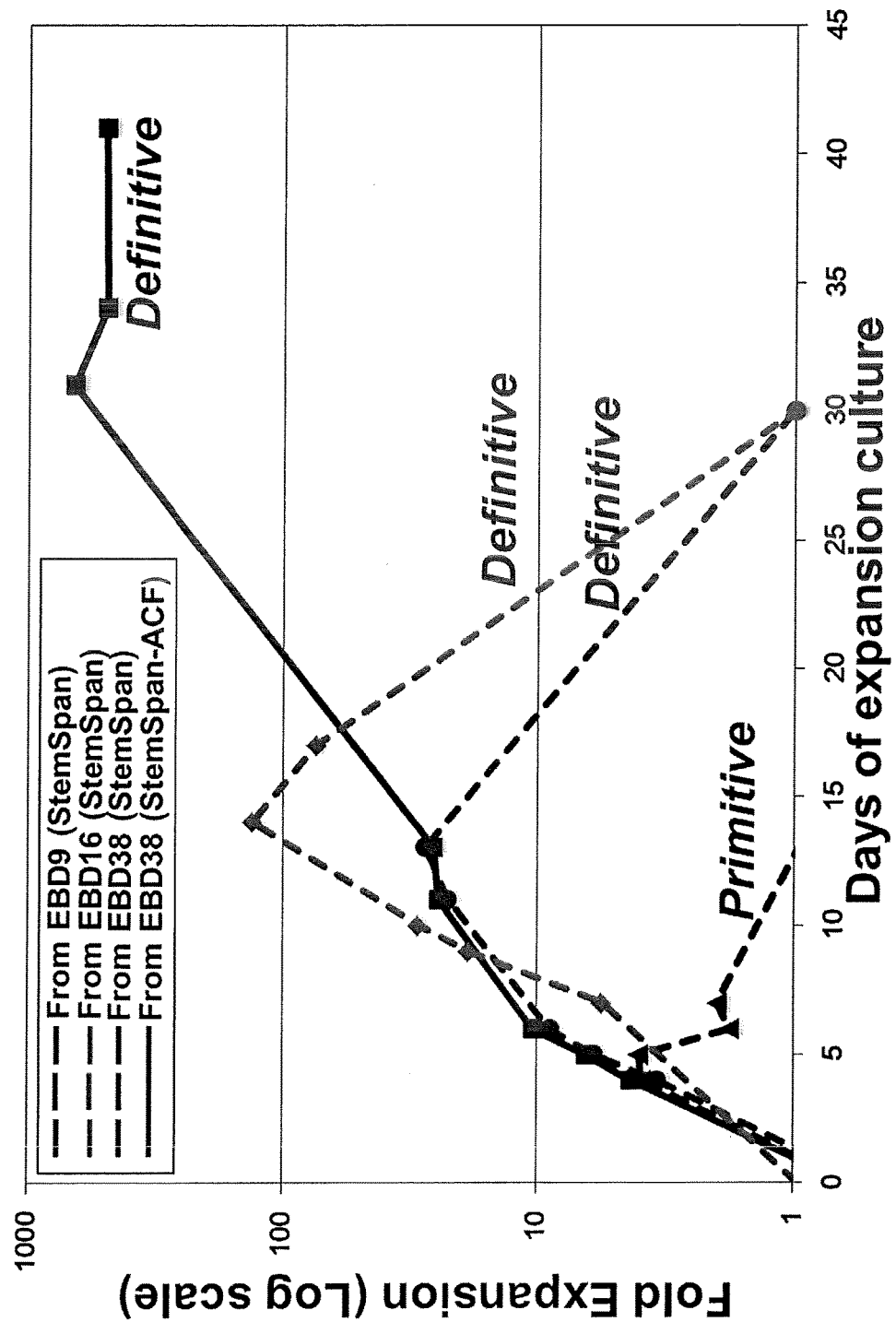
FIG. 17 is a chart showing optimalization of human culture conditions to maximize the potential to undergo extensive self-renewal. Primitive erythroid cells from embryoid body (EB) Day 9 cannot self-renew in the Expansion media (StemSpan; EPO, SCF, Dex, IGF1, ExCyte). These erythroid cells undergo terminal erythroid maturation rather than self-renewal cell divisions. Definitive erythroblasts derived from EB Day 16 or 38 in the "StemSpan media" self-renew for 2-3 weeks. Definitive erythroblasts derived from EB Day 38 in the humanized "StemSpan-ACF media" continue to self-renew for about 5-6 weeks.

The results presented herein demonstrate the importance of lipid supplementation on the self-renewal of erythroblasts. For example, it was observed that withdrawal of lipid supplements from the StemSpan expansion media slowed down erythroblast proliferation (FIG. 10). Withdrawal of lipid supplements from the StemPro34 expansion media blocked the ability of SREs to enter the "extensive" phase and become ESREs (FIG. 11). In addition, it was observed that when ESREs were cultured with or without lipid supplements for 5 days, Bmi1 transcript levels were reduced in the "no lipid" condition compared to the control culture containing lipids (FIG. 12).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of generating a substantially pure population of extensively self-renewing erythroblast (ESRE) from human cells, the method comprising:
    a) culturing human cells selected from the group consisting of human stem cells and human progenitor cells, to generate a population of definitive erythroid progenitor cells,
    b) expanding the population of definitive erythroid progenitor cells in an expansion medium comprising Epo, SCF, dexamethasone, and a lipid mixture, and providing one or more of the group consisting of Bmi-1 protein, Bmi-1 peptide, and a Bmi-1 regulating agent to the population of definitive erythroid progenitor cells in an amount sufficient for regulating erythroid self-renewal, thereby generating a substantially pure population of ESRE that undergo self-renewal cell divisions continuously for at least about 45 days, and maintains the ability to terminally mature.

2. The method of claim 1, wherein the human cells are selected from the group consisting of embryonic stem cells, induced-Pluripotent Stem (iPS) cells, adult stem cells, cord cells, bone marrow cells, and a combination thereof.

3. The method of claim 1, wherein the population of definitive erythroid progenitor cells in step a) is derived from embryoid bodies (EB).

4. The method of claim 1, wherein the cells are cultured in step a) for at least about 20 days.

5. The method of claim 1, wherein the Bmi-1 regulating agent is a hedgehog ligand.

6. The method of claim 1, wherein the expansion media is an animal component-free medium supplemented with about 2 U/mL Epo, about 100 ng/mL human recombinant SCF, about $10^{-6}$M dexamethasone, about 40 ng/mL human recombinant insulin-like growth facor-1, and about 0.4% lipid mixture.

7. A method of generating a substantially pure population of extensively self-renewing erythroblast (ESRE) from human cells, the method comprising:
    a) culturing human cells selected from the group consisting of human stem cells and human progenitor cells, in a medium comprising at least two growth factors selected from the group consisting of BMP4, VEGF, bFGF, Flt3L, SCF, IL6, TPO, IL11, IGF1 and EPO, to generate a population of definitive erythroid progenitor cells,
    b) expanding the population of definitive erythroid progenitor cells in an expansion medium comprising Epo, SCF, dexamethasone, and a lipid mixture, and providing one or more of the group consisting of Bmi-1 protein, Bmi-1 peptide, and a Bmi-1 regulating agent to the population of definitive erythroid progenitor cells in an amount sufficient for regulating erythroid self-renewal, thereby generating a substantially pure population of ESRE that undergo self-renewal cell divisions continuously for at least about 45 days, and maintains the ability to terminally mature.

* * * * *